United States Patent
Ehara

(10) Patent No.: US 7,550,623 B2
(45) Date of Patent: Jun. 23, 2009

(54) LIQUID ESTER COMPOSITIONS AND COSMETIC COMPOSITIONS CONTAINING THE SAME

(75) Inventor: Taro Ehara, Yokohama (JP)

(73) Assignee: The Nisshin OilliO Group, Ltd., Chuo-Ku, Tokyo (JP)

( * ) Notice: Subject to any disclaimer, the term of this patent is extended or adjusted under 35 U.S.C. 154(b) by 0 days.

(21) Appl. No.: 11/647,404

(22) Filed: Dec. 29, 2006

(65) Prior Publication Data

US 2007/0110702 A1 May 17, 2007

Related U.S. Application Data

(63) Continuation of application No. PCT/JP2005/012082, filed on Jun. 30, 2005.

(30) Foreign Application Priority Data

Jun. 30, 2004 (JP) ............................. 2004-194064

(51) Int. Cl.
*C07C 69/00* (2006.01)
*A61K 8/02* (2006.01)

(52) U.S. Cl. ...................... 560/129; 424/401

(58) Field of Classification Search ............ None
See application file for complete search history.

(56) References Cited

U.S. PATENT DOCUMENTS 6,444,212 B1 * 9/2002 Cavazzuti et al. ........... 424/401

FOREIGN PATENT DOCUMENTS

| JP | 55-085509 A | 6/1980 |
|----|----|----|
| JP | 62-020544 A | 1/1987 |
| JP | 1-106846 A | 4/1989 |
| JP | 2-207018 A | 8/1990 |
| JP | 4-346910 A | 12/1992 |
| JP | 8-034726 A | 2/1996 |
| JP | 9-151111 A | 6/1997 |
| JP | 2002-003340 A | 1/2002 |
| JP | 2002-316910 A | 10/2002 |
| JP | 2003-113025 A | 4/2003 |
| JP | 2003-261415 A | 9/2003 |
| JP | 2004-075639 A | 3/2004 |
| WO | 03/055451 A1 | 7/2003 |

* cited by examiner

*Primary Examiner*—Sreeni Padmanabhan
*Assistant Examiner*—Layla Soroush
(74) *Attorney, Agent, or Firm*—Buchanan Ingersoll & Rooney PC

(57) ABSTRACT

The present invention provides a liquid ester composition which is obtained by esterifying a branched isostearic acid such as 2-(1,3,3-trimethyl)butyl-5,7,7-trimethyl octanoic acid with dipentaerythritol, and said liquid ester composition having a viscosity at 25° C. of 100,000 to 2,000,000 mPa·s; hydroxyl value of 10 to 160; and cloud point of less than 5° C. This liquid ester composition has pigment dispersibility and hydrating ability that polybutene, which is one of the raw materials of oil compositions for cosmetic compositions, does not have, together with their abilities to sustain feeling of cosmetic film and improve gloss and moisture feeling of cosmetic compositions and shape retaining ability of lipsticks and the like equal to those containing polybutene.

13 Claims, No Drawings

LIQUID ESTER COMPOSITIONS AND COSMETIC COMPOSITIONS CONTAINING THE SAME

TECHNICAL FIELD OF THE INVENTION

The present invention relates to liquid ester compositions that can be used as raw materials in cosmetic compositions such as makeup, skin care and hair care products; cosmetic compositions that contain the liquid ester compositions; and lasting agents of cosmetic film that contain the liquid ester compositions.

BACKGROUND OF THE INVENTION

Up to now, in order to improve the feeling when using cosmetics, compositions for skin, and the like, especially feeling of cosmetic film, gloss, and moisture feeling, highly viscous hydrocarbon liquid oils such as wax and polybutene have been used. Since polybutene is a raw material that is excellent in improving feeling of cosmetic film and gloss and has a long-lasting feeling of cosmetic film, it is widely used in cosmetic compositions for makeup (Patent Literatures 1, 2 and 3).

However, when increasing an amount of polybutene in the cosmetic compositions in order to further improve the long-lasting feeling of cosmetic film, sticky feeling becomes stronger and the results are not always satisfactory. In addition, the hydrate ability of polybutene is very low because it is a nonpolar liquid oil. As a result, it sometimes causes make-up deterioration caused by perspiration through the skin and the like in case of formulating polybutene in cosmetic compositions or compositions for skin. Thus, polybutene is not always satisfactory in respect of making make-up last longer.

As raw materials of the cosmetic compositions that are excellent in the sense of use such as feeling of cosmetic film and richness, a polyglyceryl isostearic acid using a 2-(1,3,3-trimethyl)butyl-5,7,7-trimethyl octanoic acid as a fatty acid has been developed and reported (Patent Literature 4). However, the viscosity of the polyglyceryl isostearic acid is 35,000 mPa·s at the maximum value, and it cannot be used in cases that use of the products having the high viscosity of 100,000 mPa·s or higher is required in order to further improve functions such as pigment dispersibility and lastingness of cosmetic film.

Besides, oil solvents containing esterified compounds that are composed of multiple branched fatty acids and alcohol have been developed (Patent Literature 5). However, this literature discloses that the viscosity of the obtained esterified compounds is 30,000 mPa·s at the maximum value, and the production methods described therein sometimes generate the products having a high cloud point. Therefore, the products thus produced are not always satisfactory in respect of quality.

Further, the Patent Literature 6 discloses that a 2-(1,3,3-trimethyl)butyl-5,7,7-trimethyl octanoic acid is used as one component of an external drug wherein a medicinal drug is effectively absorbed transdermally or absorbed in the stratum corneum, but any study therein on the ester compositions obtained by esterification with alcohols has not been made.

[Patent Literature 1] Japanese Patent Unexamined Publication No. Hei 9-151111

[Patent Literature 2] Japanese Patent Unexamined Publication No. 2002-3340

[Patent Literature 3] Japanese Patent Unexamined Publication No. 2002-316910

[Patent Literature 4] Japanese Patent Unexamined Publication No. 2003-113025

[Patent Literature 5] WO03/055451 A1

[Patent Literature 6] Japanese Patent Publication No. 2-207018

DISCLOSURE OF THE INVENTION

The object of the present invention is to provide liquid ester compositions that have pigment dispersibility and hydrating ability that polybutene, which is one of the raw materials of oil compositions for cosmetic compositions, does not have, together with their abilities to sustain feeling of cosmetic film and improve gloss and moisture feeling of cosmetic compositions and shape retaining ability of lipsticks and the like equal to those containing polybutene.

The further object of the present invention is to provide cosmetic compositions that contain the above liquid ester compositions, especially the compositions for makeup.

The additional object of the present invention is to provide lasting agents of cosmetic film that contain the above liquid ester compositions.

The inventors have further thoroughly studied the inventions described in Patent Literature 5 and found that esterified compounds having a high viscosity and cloud point of less than 5° C. and of which hydroxyl value is a specific value can be obtained by reacting a specific branched isostearic acid(s) with dipentaerythritol for a long time to conduct esterification; and employing the operation of removing a low molecular substance(s) therefrom. Thus obtained esterified compounds have an excellent long-lasting feeling of cosmetic film; and pigment dispersibility and hydrating ability that polybutene does not have, together with gross and moisture feeling of cosmetic film equal to those containing polybutene, which has been usually used in cosmetic compositions. The present invention has been completed based on this finding.

Namely, the present invention provides a liquid ester composition that is obtained by esterifying a branched isostearic acid of the following chemical formula (I) with dipentaerythritol, said liquid ester composition having a viscosity at 25° C. of 100,000 to 2,000,000 mPa·s; hydroxyl value of 10 to 160; and cloud point of less than 5° C.:

wherein R represents a branched hydrocarbon group having 7 carbon atoms.

In this connection, acid value is preferably 10 or lower.

Further, the branched isostearic acid is preferably 2-(1,3,3-trimethyl)butyl-5,7,7-trimethyl octanoic acid.

The present invention also provides a cosmetic composition that contains the above-mentioned liquid ester composition.

Here, the cosmetic composition is preferably one kind selected from the group consisting of cosmetic compositions for makeup, emulsions, cream, sunscreen agents and cosmetic compositions for hair.

The present invention further provides a cosmetic composition for makeup that contains the above-mentioned liquid ester composition and an oil gelator(s).

The present invention additionally provides a lasting agents of cosmetic film that contains the above-mentioned liquid ester composition.

BEST MODE FOR CARRYING OUT THE INVENTION

First, the liquid ester compositions of the present invention are described as follows.

A branched isostearic acid used in the present invention is represented by the above-mentioned formula (I), wherein the branched hydrocarbon group having 7 carbon atoms represented by R is preferably a branched alkyl group, and an end thereof is preferably a tertiary alkyl group. Particularly, the end thereof is preferably a t-butyl group. More specifically, a 4,4-dimethylpentyl group, 1,3,3-trimethylbutyl group and 2,3,3-trimethylbutyl group are preferable. Among them, a 1,3,3-trimethylbutyl group is particularly preferable. More specifically, it includes a 2-(1,3,3-trimethyl)butyl-5,7,7-trimethyl octanoic acid and the like. As for the branched isostearic acid, marketed products thereof can be used. For example, there is Isostearic Acid, the product produced by Nissan Chemical Industries, Ltd.

As for dipentaerythritol used in the present invention, marketed products thereof can be used. For example, there are Dipentaerythritol produced by Koei Chemical Co., Ltd., and Dipentaerythritol produced by Perstorp AB.

The liquid ester compositions of the present invention are mixtures of two or more kinds selected from group consisting of monoester, diester, triester, tetraester, pentaester and hexaester of dipentaerythritol.

The liquid ester compositions of the present invention have a viscosity at 25° C. of 100,000 to 2,000,000 mPa·s, preferably 110,000 to 1,000,000 mPa·s, and most preferably 150,000 to 600,000 mPa·s. The viscosity within the above range is preferable because cosmetic film that adheres to skin well is formed in using such a liquid ester composition(s) in cosmetic compositions, and feeling of the cosmetic film is sustained, and, therefore, it is possible to obtain the cosmetic compositions that are satisfactory in respect of making make-up last longer. In addition, the sense of use and gloss thereof are satisfactory because they are satisfactory in respect of making make-up last longer due to the excellent lastingness of the cosmetic film, together with the excellent coating properties and uniform formulation of cosmetic film.

The viscosity of the liquid ester compositions of the present invention can be determined by the Viscosity Determination Method II in General Tests in the Standards of Cosmetic Ingredients (Brookfield Viscometer (Type BH)).

The liquid ester compositions of the present invention have a hydroxyl value of 10 to 160, preferably 20 to 140 and most preferably 25 to 95. The hydroxyl value within the above range is preferable because the compositions have an excellent long-lasting feeling of cosmetic film and moisture feeling and do not cause makeup deterioration, and, therefore, it is possible to obtain the cosmetic compositions that are satisfactory in respect of making make-up last longer. Besides, it is also possible to obtain the cosmetic compositions that are satisfactory in respect of temporal stability because they have excellent coating properties and neither increase sticky feeling in coating nor cause decrease in transparency and precipitation of solid contents.

The hydroxyl value can be determined by the Hydroxyl Value Determination in General Tests in the Standards of Cosmetic Ingredients.

The liquid ester compositions of the present invention have a cloud point of less than 5° C., preferably not more than 0° C. and more preferably not more than −20° C. The cloud point within the above range is preferable because appearance of the products can be well maintained in respect of transparency even under low temperature.

The cloud point can be determined by the Cloud Point Determination in General Tests in the Standards of Cosmetic Ingredients.

The liquid ester compositions of the present invention preferably have an acid value of 10 or lower, more preferably 5 or lower and most preferable 0 to 1. The acid value within the above range is preferable because stimulation to skin is lowered, preservation stability is good, and sticky feeling can be controlled.

The acid value can be determined by the Acid Value Determination in General Tests in the Standards of Cosmetic Ingredients.

Next, methods for producing the liquid ester compositions of the present invention are described as follows.

The liquid ester compositions of the present invention can be produced by esterifying the branched isostearic acid of the above-mentioned formula (I) with dipentaerythritol.

More specifically, for example, it is preferably produced by the method comprising the following steps. Dipentaerythritol and a 2-(1,3,3-trimethyl)butyl-5,7,7-trimethyl octanoic acid are set in the mass ratio of 10:35 to 10:90, and esterification reaction is conducted at 200 to 250° C. for 10 to 40 hours, preferably 20 to 40 hours, at the presence of a suitable amount of a catalyst(s) (such as 0.02 to 0.5% of dibutyltin oxide to the total set amount). After the completion of the reaction, the obtained reactant is subjected to operations such as the adsorption treatment to conduct removal of the catalyst(s). Then, after cooling down the reactant to 70° C. or lower (for example, 50 to 60° C.), it is filtered and low molecules such as unreacted raw materials are removed by distilment and the like.

The mass ratio of the raw materials of each dipentaerythritol and the branched isostearic acid that are set (a value of dipentaerythritol: the branched isostearic acid) is preferably 10:35 to 10:90, more preferably 10:39 to 10:72 and most preferably 10:48 to 10:70.

Next, the cosmetic compositions that contain the liquid ester compositions of the present invention are described as follows.

The content of the liquid ester compositions in the cosmetic compositions is preferably 0.1 to 90 mass %, more preferably 0.5 to 80% and most preferably 10 to 80 mass %.

The cosmetic compositions that contain the liquid ester compositions of the present invention are not particularly limited, and they include cosmetic compositions for makeup, emulsions, cream, sunscreen agents and cosmetic compositions for hair, for example. Since the functions such as a long-lasting feeling of cosmetic film, gloss, pigment dispersibility, hydrating ability and moisturizing effect are particularly required, it is effective in using them to cosmetic compositions for makeup, emulsions, cream, sunscreen agents and cosmetic compositions for hair.

Here, the cosmetic compositions for makeup mean lipsticks, lip gloss, lip salves, foundation, blusher, eye gloss, eye shadow, eyeliner, mascara and nail polish. The cosmetic compositions for hair mean hair cream, hair liquid, hair styling mousse, hair setting gel and hair styling wax.

In the cosmetic compositions that contain the liquid ester compositions of the present invention, the objective products can be produced in accordance with ordinary methods, by blending various components usually used in the cosmetic compositions within the embodiment that does not deteriorate the effects of the present invention, if necessary.

For example, it is possible to arbitrarily blend anion surfactants, cation surfactants, ampholytic surfactants, lipophilic nonionic surfactants, hydrophilic nonionic surfactants, natural surfactants, liquid fats and oils, solid fats and oils, waxes, hydrocarbon oils, higher fatty acids, higher alcohols, ester oils, silicon oils, powders, moisturizers, natural water-soluble polymers, semisynthetic water-soluble polymers, synthetic water-soluble polymers, inorganic water-soluble polymers, thickeners, ultraviolet absorbers, chelating agents, lower alcohols, polyalcohols, monosaccharides, oligosaccharides, polysaccharides, amino acids, organic amines, synthetic-resin emulsions, pH adjuster, vitamins, antioxidants, antioxidizing auxiliaries, fragrances and water, if necessary.

Examples of anion surfactants include one or more kinds selected from fatty-acid soaps such as substrates for soap, sodium laurate and sodium palmitate; salts of higher alkyl sulfuric ester such as sodium lauryl sulfate and potassium lauryl sulfate; salts of alkyl ether sulfuric ester such as POE-triethanolamine lauryl sulfate and POE-sodium lauryl sulfate; N-acylsarcosine acids such as sodium lauroyl sarcosine; higher fatty acid amide sulfonates such as sodium N-myristoyl-N-methyl taurate, sodium palm oil fatty acid methyl tauride and sodium lauryl methyl tauride; salts of phosphoric ester such as sodium POE-oleyl ether phosphate and POE-stearyl ether phosphoric acid; sulfosuccinates such as sodium di-2-ethylhexyl sulfosuccinate, sodium monolauroyl monoethanolamide polyoxyethylene sulfosuccinate and sodium lauryl polypropylene glycol sulfosuccinate; alkylbenzene sulfonates such as sodium linear dodecylbenzenesulfonate, linear triethanolamine dodecylbenzenesulfonate and linear dodecylbenzenesulfonic acid; N-acylglutamates such as monosodium N-lauroyl glutamate, disodium N-stearoyl glutamate and monosodium N-myristoyl-L-glutamate; higher fatty acid ester sulfates such as hardening palm oil fatty acid glycerin sodium sulfate; sulfated oils such as sulfated caster oil; POE-alkylether carboxylic acids; POE-alkylallyl ether carboxylate; α-olefin sulfonate; higher fatty acid ester sulfonate; secondary alcohol sulfates; higher fatty acid alkylol amide sulfates; sodium lauroyl monoethanolamide succinate; ditriethanolamine N-palmitoyl aspartate; and casein sodium.

Examples of cation surfactants include one or more kinds selected from alkyltrimethyl ammonium salts such as stearyl trimethyl ammonium chloride and lauryl trimethyl ammonium chloride; alkylpyridinium salts such as distearyl dimethyl ammonium chloride dialkyl dimethyl ammonium salts, poly(N,N'-dimethyl-3,5-methylene piperidinium) chloride and cetylpyridinium chloride; alkyl quaternary ammonium salts, alkyl dimethyl benzyl ammonium salts, alkyl isoquinolinium salts, dialkyl morphonium salts, POE-alkylamine, alkylamine salts, polyamine fatty acid derivatives, amyl alcohol fatty acid derivatives, benzalkonium chloride and benzetonium chloride.

Examples of ampholytic surfactants include one or more kinds selected from imidazoline ampholytic surfactants such as sodium 2-undecyl-N,N,N-(hydroxyethyl carboxymethyl)-2-imidazoline and salts of disodium 2-cocoyl-2-imidazolinium hydroxide-1-carboxyethyloxy; and betaine ampholytic surfactants such as 2-heptadecyl-N-carboxymethyl-N-hydroxyethyl imidazolinium betaine, lauryl dimethylamino acetic acid betaine, alkyl betaine, amido betaine and sulfobetaine.

Examples of lipophilic nonionic surfactants include one or more kinds selected from sorbitan fatty acid esters such as sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate and tetra-2-ethylhexyl diglycerol sorbitan; glycerin fatty acids esters such as mono cottonseed oil fatty acid glycerin ester, mono erucic acid glycerin ester, sesquioleic acid glycerin ester, monostearic acid glycerin ester, α, α'-oleic acid pyroglutamic acid glycerin ester and monostearic acid glycerin ester; polyglycerin fatty acid esters such as diglyceryl monoisostearate and diglyceryl diisostearate; propylene glycol fatty acid esters such as propylene glycol monostearate; hardened castor oil derivatives; and glycerin alkylether.

Examples of hydrophilic nonionic surfactants include one or more kinds selected from POE-sorbitan fatty acid esters such as POE-sorbitan monooleate, POE-sorbitan monostearate, POE-sorbitan monooleate and POE-sorbitan tetraoleate; POE-sorbit fatty acid esters such as POE-sorbit monolaurate, POE-sorbit monooleate, POE-sorbit pentaoleate, POE-sorbit monostearate; POE-glycerin fatty acid esters such as POE-glycerin monostearate, POE-glycerin monoisostearate and POE-glycerin triisostearate; POE-fatty acid esters such as POE-monooleate, POE-distearate, POE-monodioleate and distearic acid ethylene glycol; POE-alkylethers such as POE-laurylether, POE-oleylether, POE-stearylether, POE-behenylether, POE-2-octyldodecylether and POE-cholestanolether; pluronic types such as pluronic; POE•POP-alkylethers such as POE•POP-cetylether, POE•POP-2-decyltetradecylether, POE•POP-monobutylether, POE•POP-hydrogenated lanolin and POE•POP-glycerinether; tetra POE•tetra POP-ethylenediamine condensation products such as tetronic; POE-castor oil hardened castor oil derivatives such as POE-castor oil, POE-hardened castor oil, POE-hardened castor oil monoisostearate, POE-hardened castor oil triisostearate, POE-hardened castor oil monopyroglutamic acid monoisostearic acid diester and POE-hardened castor oil maleic acid; POE-beeswax-lanolin derivatives such as POE-sorbit beeswax; alkanolamides such as palm oil fatty acid diethanolamide, monoethanolamide laurate and fatty acid isopropanolamide; POE-propylene glycol fatty acid esters; POE-alkylamines; POE-fatty acid amides; sucrose fatty acid esters; POE-nonylphenyl formaldehyde condensation products; alkylethoxy dimethyl amine oxides and trioleyl phosphoric acids.

Examples of natural surfactants include one or more kinds selected from lecithins such as soybean phospholipids, hydrogenated soybean phospholipids, egg yolk phospholipids and hydrogenated egg yolk phospholipids; and soybean saponins.

Examples of liquid fats and oils include one or more kinds selected from avocado oil, camellia oil, turtle oil, macadamia nut oil, corn oil, sunflower oil, mink oil, olive oil, canola oil, egg yolk oil, sesame seed oil, persic oil, wheat germ oil, sasanqua oil, castor oil, linseed oil, safflower oil, grapeseed oil, cottonseed oil, perilla oil, soybean oil, earthnut oil, tea seed oil, torreya seed oil, rice bran oil, aleurites fordii oil, Japanese tung oil, jojoba oil, germ oil, evening primrose oil, trioctanoic acid glycerin and triisopalmitic acid glycerin. Here, the liquid fats mean liquid fats and oils at room temperature.

Examples of solid fats and oils include one or more kinds selected from cacao butter, palm oil, beef tallow, mutton tallow, horse fat, palm kernel oil, lard, beef bone fat, tree wax kernel oil, hoof oil, tree wax, hardened palm oil, hardened palm oil, hardened beef tallow, hardened oil and hardened castor oil.

Examples of waxes include one or more kinds selected from beeswax, candelilla wax, cotton wax, carnauba wax, bayberry wax, Ibota wax, whale wax, montan wax, rice bran wax, kapok wax, sugarcane wax, lanolin, acetylated lanolin, liquid lanolin, isopropyl lanolate, reduced lanolin, hard lanolin, hexyl laurate, jojoba wax, shellac wax, POE lanolin alcohol ether, POE lanolin alcohol acetate, POE cholesterol ether, lanolin fatty acid polyethylene glycol and POE hydrogenated lanolin alcohol ether.

Examples of hydrocarbon oils include one or more kinds selected from liquid paraffin, isoparaffin, heavy liquid isoparaffin, paraffin, ozocerite, squalane, vegetable squalane, pristine, ceresin, squalene, vaseline, microcrystalline wax, paraffin wax, montan wax, olefin oligomer, polyisobutylene, polybutene and hydrogenated polybutene.

Examples of higher fatty acids include one or more kinds selected from lauric acid, myristic acid, palmitic acid, stearic acid, behenic acid, oleic acid, undecylenic acid, tall oil acid, isostearic acid, linoleic acid, linolenic acid, eicosapentaenoic acid (EPA) and docosahexaenoic acid (DHA).

Examples of higher alcohols include one or more kinds selected from linear alcohols such as lauryl alcohol, cetyl alcohol, stearyl alcohol, behenyl alcohol, myristyl alcohol, oleyl alcohol, setostearyl alcohol; and branched alcohols such as monostearyl glycerin ether (batyl alcohol), 2-decyl tetra decynol, lanolin alcohol, cholesterol, phytosterol, hexyl dodecanol, isostearic alcohol and octyl dodecanol.

Examples of ester oils include one or more kinds selected from isopropyl myristate, cetyl isooctanoate, octyldodecyl myristate, isopropyl palmitate, isooctyl palmitate, butyl stearate, hexyl laurate, myristyl myristate, decyl oleate, hexyldecyl dimethyl octanoate, cetyl lactate, myristyl lactate, octyldodecyl lactate, acetylated lanolin, isocetyl stearate, isocetyl isostearate, cholesteryl 12-hydroxy stearate, phytosteryl 12-hydroxy stearate, phytosteryl oleate, ethylene glycol di-2-ethylhexanoate, propylene glycol dicaprate, dipentaerythritol fatty acid ester, N-alkyl glycol monoisostearate, neopentyl glycol dicaprate, diisostearyl malate, glycerin di-2-heptyl undecanoate, trimethylolpropane tri-2-ethylhexanoate, trimethylolpropane triisostearate, pentaerythritol tetra-2-ethylhexanoate, glyceryl tri-2-ethylhexanoate, tri(capryl/capric acid) glyceryl ester, tri(capryl/caprin/myristin/stearic acid) glyceride, trimethylolpropane triisostearate, cetyl 2-ethylhexanoate, 2-ethylhexylpalmitate, glycerin trimyristate, tri-2-heptyl undecanoic acid glyceride, polyglyceryl diisostearate, polyglyceryl triisostearate, polyglyceryl tetraisostearate, diglyceryl triisostearate, diglyceryl tetraisostearate, erythrityl tri2-ethylhexanoate, ditrimethylolpropane tri2-ethylhexanoate, (isostearic acid/sebacic acid) ditrimethylolpropane oligoester, castor oil fatty acid methylester, oleyl oleate, acetoglyceride, 2-heptyl undecyl palmitate, diisobutyl adipate, (adipic acid/2-ethylhexanoic acid/stearic acid) glycerin oligoester, (2-hexyl decanoic acid/sebacic acid) diglyceryl oligoester, N-lauroyl-L-glutamic acid-2-octyldodecylester, di-2-heptyl undecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, ethyl acetate, butyl acetate and triethyl citrate.

Examples of silicon oils include one or more kinds selected from chain polysiloxanes such as dimethyl polysiloxane, methylphenyl polysiloxane and methylhydrogen polysiloxane; cyclic polysiloxanes such as octamethylcyclotetrasiloxane, decamethylcyclopentasiloxane, dodecamethylcyclohexasiloxane and tetrahydrotetramethylcyclotetrasiloxane; and polyoxyethylene polyalkyl siloxane.

Usability of the cosmetic compositions can be improved and toning thereof can be adjusted by adding powders. The powders that can be used are not particularly limited by forms such as spherical, plate and needle shapes; particle sizes such as fumy particles, fine particles and pigments; and particle structures such as porous and non-porous structures, and inorganic powders, photoluminescent powders, organic powders, pigment powders, metal powders and compound powders can be used. Specific examples of the powders include white inorganic pigments such as titanium oxide, zinc oxide, cerium oxide and barium sulfate; colored inorganic pigments such as ferric oxide, titanic iron, γ-ferric oxide, iron oxide yellow, iron oxide black, carbon black, low-dimensional titanic oxide, chrome oxide, chromium hydroxide, iron blue, cobalt blue, yellow ocher, mango violet, cobalt violet and titanic cobalt; white body powders such as talc, mica, white mica, gold mica, red mica, black mica, synthesized mica, sericite, lithia mica, vermiculite, synthesized sericite, kaolin, silicon carbide, bentonite, smectite, aluminum oxide, magnesium oxide, zirconium oxide, antimony oxide, diatom earth, aluminum silicate, magnesium aluminum metasilicate, calcium silicate, barium silicate, magnesium silicate, strontium silicate, metal salts of tungsten acid, calcium phosphate, calcium carbonate, magnesium carbonate, calcined calcium sulfate, apatite fluoride, hydroxyapatite, silica, zeolite, ceramic powder and boric acid nitriding; photoluminescent powders such as titanium dioxide coated mica, titanium dioxide coated talc, titanium dioxide coated bismuth oxychloride, colored titanium oxide coated mica, ferric oxide mica titanium, iron blue treated mica titanium, carmine treated mica titanium, bismuth oxychloride, argentine, polyethylene telephthalate/aluminum/epoxy laminated powder and polyethylene telephthalate/polyolefin laminated powder; copolymer resins such as polyamide resins, polyethylene resins, polyacryl resins, polyester resins, fluorine resins, cellulose resins, polystyrene resins and styrene-acryl copolymer resins; organic polymer resin powders such as polypropylene resins, silicon resins, urethane resins, benzoguanamine resins and polyethylene tetrafluoride resins; organic low molecular powders such as zinc myristate, zinc stearate, calcium palmitate, aluminum stearate and N-acyllysine; natural organic powders such as starch, silk powder and cellulose powder; organic pigment powders such as Red No. 201, Red No. 202, Red No. 205, Red No. 220, Red No. 226, Red No. 228, Red No. 405, Orange No. 203, Orange No. 204, Blue No. 404, Yellow No. 205 and Yellow No. 401; organic pigment powders such as zirconium, barium and aluminum lake, e.g. Red No. 3, Red No. 104, Red No. 106, Red No. 227, Red No. 230, Red No. 401, Red No. 505, Orange No. 205, Yellow No. 4, Yellow No. 5, Yellow No. 202, Yellow No. 203, Green No. 3 and Blue No. 1; or, further, metal powders such as aluminum powder, magnesium powder, copper powder, gold powder and silver powder; and compound powders such as particulate titanium oxide coated mica titanium, particulate zinc oxide coated mica titanium, barium sulfate coated mica titanium, silicon dioxide containing titanium oxide and silicon dioxide containing zinc oxide. These powders can be used by itself or two or more kinds thereof, and a complex compound(s) thereof can also be used. These powders can be used, of which surface is treated by using one or more kinds selected from fluorine compounds, silicon compounds, metal soaps, lecithins, hydrogenated lecithins, collagen, hydrocarbons, higher fatty acids, higher alcohols, esters, waxes, and surfactants.

Examples of moisturizers include one or more kinds selected from polyethylene glycol, propylene glycol, glucerine, 1,3-butylene glycol, xylitol, sorbitol, maltitol, chondroitin sulfuric acid, hyaluronic acid, mucoitinsulfuric acid, Trichosanthis Semen acid, atelocollagen, cholesteryl-12-hydroxy stearate, sodium lactate, urea, bile salt, dl-pyrrolidone carboxylate, short-chain soluble collagen, diglycerin (EO) PO adducts, rosa roxburghii, yarrow extracts and melilot extracts.

Examples of natural water-soluble polymers include one or more kinds selected from plant polymers such as gum arabic, gum tragacanth, galactan, guar gum, carob gum, Karaya gum, carrageenan, pectin, agar, quince seed (marmelo), algae colloid (brown algae extracts) and starch (rice, corn, potato, wheat); microbial polymers such as xanthan gum, dextran, succinoglucan and pullulan; and animal polymers such as collagen, casein, albumin and gelatin.

Examples of semisynthetic water-soluble polymers include one or more kinds selected from starch polymers such as carboxymethyl starch and methylhydroxypropyl starch; cellulose polymers such as methyl cellulose, nitrocellulose, methylhydroxypropyl cellulose, cellulose sodium sulfate, hydroxypropyl cellulose, carboxymethyl cellulose, sodium carboxymethyl cellulose, crystalline cellulose and cellulose powder; and alginic acid polymers such as sodium alginate and alginic acid propylene glycol ester.

Examples of synthetic water-soluble polymers include one or more kinds selected from vinyl polymers such as polyvinyl alcohol, polyvinyl methyl ether, polyvinyl pyrrolidone and carboxyvinyl polymer (carbopol); polyoxyethylene polymers such as polyethylene glycol 20,000, 40,000 and 60,000; acrylic polymers such as polyoxyethylene polyoxypropylene copolymer copolymerized polymer, polyacrylic acid sodium, polyethyl acrylate and polyacrylamide; and polyethylene imine and cation polymer.

Examples of inorganic water-soluble polymers include one or more kinds selected from bentonite, AlMg silicate (bee gum), laponite, hectorite and anhydrous silicic acid.

Examples of thickeners include one or more kinds selected from gum arabic, carrageenan, Karaya gum, gum tragacanth, carob gum, quince seed (marmelo), casein, dextrin, gelatin, sodium pectin acid, sodium alginate, methylcellulose, ethylcellulose, CMC, hydroxyethyl cellulose, hydroxypropyl cellulose, PVA, PVM, PVP, sodium polyacrylate, carboxyvinyl polymer, locust bean gum, guar gum, tamarind gum, dialkyl dimethyl ammonium cellulose sulfate, xanthan gum, magnesium aluminum silicate, bentonite and hectorite.

Examples of ultraviolet absorbers include one or more kinds selected from benzoic acid ultraviolet absorbers such as para-aminobenzoic acid (hereinafter abbreviated as PABA), PABA monoglycerin ester, N,N-dipropoxy PABA ethyl ester, N,N-diethoxy PABA ethyl ester, N,N-dimethyl PABA ethyl ester, N,N-dimethyl PABA butyl ester and N,N-dimethyl PABA ethyl ester; anthranilic acid ultraviolet absorbers such as homomenthyl-N-acetylanthranilate; salicylic acid ultraviolet absorbers such as amyl salicylate, menthyl salicylate, homomenthyl salicylate, octyl salicylate, phenyl salicylate, benzyl salicylate and p-isopropanol phenyl salicylate; cinnamic acid ultraviolet absorbers such as octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxycinnamate, isopropyl-p-methoxycinnamate, isoamyl-p-methoxycinnamate, octyl-p-methoxycinnamate (2-ethylhexyl-p-methoxycinnamate), 2-ethoxyethyl-p-methoxycinnamate, cyclohexyl-p-methoxycinnamate, ethyl-α-cyano-β-phenyl cinnamate, 2-ethylhexyl-α-cyano-β-phenyl cinnamate and glyceryl mono-2-ethylhexanoyl-diparamethoxycinnamate; benzophenone ultraviolet absorbers such as 2,4-dihydroxybenzophenone, 2,2'-dihydroxy-4-methoxybenzophenone, 2,2'-dihydroxy-4,4'-dimethoxybenzophenone, 2, 2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenyl-benzophenone-2-carboxylate, 2-hydroxy-4-n-octoxybenzophenone and 4-hydroxy-3-carboxybenzophenone; 3-(4'-methylbenzylidene)d,l-camphor; 3-benzylidene-d,l-camphor; urocanic acid, urocanic acid ethyl ester; 2-phenyl-5-methylbenzoxazole; 2,2'-hydroxy-5-methylphenyl benzotriazole; 2-(2'-hydroxy-5'-t-octylphenyl)benzotriazole; 2-(2'-hydroxy-5'-methylphenyl)benzotriazole; dibenzalazine; dianisoylmethane; 4-methoxy-4'-t-butyl dibenzoylmethane; 5-(3,3-dimethyl-2-norbornylidene)-3-pentane-2-one; and 2,4,6-trianilino-p-(carbo-2'-ethylhexyl-1'-oxy)1,3,5-triazine.

Examples of sequestrants include one or more kinds selected from 1-hydroxyethane-1,1-diphosphonate, tetrasodium salt of 1-hydroxyethane-1,1-diphosphonate, disodium edentate, edetate trisodium, edentate tetrasodium, sodium citrate, sodium polyphosphate, sodium metaphosphate, gluconic acid, phosphoric acid, citric acid, ascorbic acid, succinic acid, edetic acid and trisodium ethylenediamine hydroxyethyl triacetate.

Examples of lower alcohols include one or more kinds selected from methanol, ethanol, propanol, isopropanol, isobutyl alcohol and t-butyl alcohol.

Examples of polyalcohols include one or more kinds selected from dihydric alcohols such as ethylene glycol, propylene glycol, trimethylene glycol, 1,2-butylene glycol, 1,3-butylene glycol, tetramethylene glucol, 2,3-butylene glucol, pentamethylene glucol, 2-butene-1,4-diol, hexylene glycol and octylene glycol; trihydric alcohols such as glycerin, trimethylolpropane and 1,2,6-hexanetriol; tetrahydric alcohols such as pentaerythritol; pentahydric alcohols such as xylitol; hexahydric alcohols such as sorbitol and mannitol; polyalcohol polymers such as diethylene glycol, dipropylene glycol, triethylene glucol, polypropylene glycol, tetraethylene glycol, diglycerin, polyethylene glycol, triglycerin, tetraglycerin and polyglycerin; dihydric alcoholic alkyl ethers such as ethylene glycol monomethyl ether, ethylene glucol monoethyl ether, ethylene glycol monobutyl ether, ethylene glycol monophenyl ether, ethylene glycol monohexyl ether, ethylene glycol mono 2-methylhexyl ether, ethylene glycol isoamyl ether, ethylene glycol benzyl ether, ethylene glycol isopropyl ether, ethylene glycol dimethyl ether, ethylene glycol diethyl ether and ethylene glycol dibutyl ether; dihydric alcohol alkyl ethers such as diethylene glycol monomethyl ether, diethylene glucol monoethyl ether, diethylene glycol monobutyl ether, diethylene glycol dimethyl ether, diethylene glycol diethyl ether, diethylene glycol butyl ether, diethylene glycol methylethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether and dipropylene glycol butyl ether; dihydric alcohol ether esters such as ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate and propylene glycol monophenyl ether acetate; glycerin monoalkyl ethers such as xyl alcohol, selachyl alcohol and batyl alcohol; sugar alcohols such as sorbitol, maltitol, maltotriose, mannitol, lactitol, sucrose, erythritol, glucose, fructose, amylolytic sugar, maltose, xylitose and amylolytic sugar reducing alcohol; glysolid; tetrahydroflufuryl alcohol; POE-tetrahydroflufuryl alcohol; POP-butyl ether; POP/POE-butyl ether; tripolyoxy propylene glycerin ether; POP-glycerin ether; POP-glycerin ether phosphoric acid; and POP/POE-pentane erythritol ether.

Examples of monosaccharides include one or more kinds selected from trioses such as D-glyceryl aldehyde and dihydroxy acetone; tetroses such as D-erythrose, D-erythrulose, D-threose and erythritol; pentoses such as L-arabinose, D-xylose, L-lyxose, D-arabinose, D-ribose, D-ribulose, D-xylulose and L-xylulose; hexoses such as D-glucose, D-talose, D-psicose, D-galactose, D-fructose, L-galactose, L-mannose, and D-tagatose; heptoses such as aldoheptose and heptrose; octoses such as octrose; deoxy sugars such as 2-deoxy-D-ribose, 6-deoxy-L-galactose and 6-deoxy-L-mannose; amino sugars such as D-glucosamine, D-galactosamine, sialic acid, amino uronic acid and muramic acid; and uronic acids such as D-glucuronic acid, D-mannuronic acid, L-guluronic acid, D-galacturonic acid and L-iduronic acid.

Examples of oligosaccharides include one or more kinds selected from sucrose, gunchianose, umbelliferose, lactose, planteose, isolignoses, α, α-trehalose, raffinose, lignoses, umbilicine and stachyose verbascoses.

Examples of polysaccharides include one or more kinds selected from cellulose, quince seed, chondroitin sulfuric acid, starch, dextrin, glucomannan, chitin, galactan, dermatan sulfuric acid, glycogen, gum arabic, heparin sulfuric acid, hyaluronic acid, gum tragacanth, keratan sulfuric acid, chondroitin, xanthan gum, mucoitinsulfuric acid, guar gum, dextran, keratosulfuric acid, locust bean gum, succinoglucan and Trichosanthis Semen acid.

Examples of amino acids include neutral amino acids such as threonine and cysteine; and basic amino acids such as hydroxylysine. Further, amino acid derivatives include one or more kinds selected from sodium acylsarcosine (sodium lauroylsarcosine), acyl glutamate, acyl β-alanine sodium, glutathione and pyrrolidone carboxylic acid.

Examples of organic amines include one or more kinds selected from monoethanolamine, diethanolamine, triethanolamine, morpholine, triisopropanolamine, 2-amino-2-methyl-1,3-propanediol and 2-amino-2-methyl-1-propanol.

Examples of synthetic-resin emulsions include one or more kinds selected from acrylic resin emulsion, polyacrylic acid ethyl emulsion, acrylic resin solution, polyacryl alkyl ester emulsion and polyvinyl acetate resin emulsion.

Examples of the pH adjusters include one or more kinds selected from buffers such as lactic acid—sodium lactate and citric acid—sodium citrate.

Examples of vitamins include one or more kinds selected from vitamin A, vitamin B1, vitamin B2, vitamin B6, vitamin E, vitamin K and derivatives thereof; pantothenic acids and derivatives thereof; and biotins.

Examples of antioxidants include one or more kinds selected from tocopherols, dibutyl hydroxytoluene, butylhydroxyanisol and gallic acid esters.

Examples of antioxidizing auxiliaries include one or more kinds selected from phosphoric acids, citric acids, ascorbic acids, maleic acids, malonic acids, succinic acids, fumaric acids, cephalin, hexametaphosphate, phytic acid and ethylenediamine tetraacetic acid.

Examples of the other components that can be added to the cosmetic compositions include one or more kinds selected from antiseptic agents such as ethylparaben and butylparaben; ultraviolet absorbers such as benzophenone derivatives, PABA derivatives, cinnamic acid derivatives, salicylic acid derivatives, 4-tert-butyl-4'-methoxydibenzoylmethane and oxybenzone; antiflash agents such as glycyrrhizinic acid derivatives, glycyrrhetinic acid derivatives, salicylic acid derivatives, hinokitiol, zinc oxide and allantoin; skin whitening agents such as placental extracts and saxifragaceous extracts; extracts of cork tree bark, coptis root, lithospermi radix, peony root, swertia herb, birch, sage, loquat, carrots, aloe, tree mallow, iris, grapes, coix seed, loofah, lily, saffron, Cnidium Rhizome, ginger, hypericum, ononis, garlic, capsicum, citrus unshiu peel, Japanese angelica root and seaweed; activator agents such as royal jelly, photosensitive pigments, cholesterol derivatives and infant blood extracts; blood circulation promoters such as 4-hydroxy-3-methoxybenzyl nonylic acid amide, nicotinic acid benzyl ester, nicotinic acid β-butoxy ethyl ester, capsaicin, gingerone, cantharides tincture, ichthammol, tannic acid, α-borneol, nicotinic acid tocopherol, inositol hexanicotinate, cyclandelate, cinnarizine, tolazoline, acetylcholine, verapamil, cepharanthine, γ-orizanol; antiseborrheic agents such as sulfur and thianthol; tranexamic acids; thiotaurine; and hypotaurine.

Besides, an oil gelator(s) can be contained in the cosmetic compositions of the present invention. The make-up compositions containing a liquid ester composition(s) and an oil gelator(s) are particularly excellent in sense of use, and shape retaining ability and preservation stability thereof are high.

The shape retaining ability and gelation ability are synergistically improved by combining the liquid ester compositions of the present invention with the gelators, feeling of cosmetic film is sustained, and, therefore, make-up compositions that make make-up last longer can be obtained.

Here, the oil gelators in the present invention mean those that can solidify or gelatinize oily components such as fats and oils, waxes, hydrocarbon oils, higher fatty acids, higher alcohols, ester oils and silicon oils, and marketed products thereof can be used.

The oil gelators include waxes, 12-hydroxystearic acid, dextrin fatty acid esters, sucrose fatty acid esters, metal soaps, anhydrous silicic acids, (behenic acid/eicosanic diacid) glyceryl and organically modified clay minerals. It is possible to use one or more kinds selected from the above.

Waxes that are the oil gelators include paraffin wax, ceresin wax, microcrystalline wax, Fischer-Tropsch wax, polyethylene wax, carnauba wax and candelilla wax, and one or more kinds selected from the above can be used.

The marketed products thereof include trade name: Purified Carnauba Wax No. 1, produced by Noda Wax Co., Ltd.; trade name: OZOKERAITE WAX SP-273P, produced by STRAHL & PITSH INC.; trade name: Microwax 190Y, produced by Mobil Oil Co.; trade name: Himic 1080/2095, produced by Nippon Seiro Co., Ltd.; trade name: Sanwax E-200/E-300, produced by Sanyo Chemical Industries, Ltd.; trade name: Mobil 180, produced by Mobil Oil Co.; trade name: Starwax 100, produced by Bareco; trade name: Nisseki Microwax 180, produced by Nippon Oil Corporation; trade name: Fischer-Tropsch Wax FT-95/FT100H/FT-150/FT-200, produced by Sasol Wax Limited; trade name: BeSquare 180/185/190/195, produced by Bareco; trade name: Polywax 500/655, produced by Bareco; and trade name: Sasol Wax H1/C1/C2, produced by Sasol Wax Limited.

12-hydroxystearic acid that is the oil gelator is a fatty acid having hydroxyl group. It can be obtained by hydrogenating a recinoleic acid that is obtained from castor oil.

Dextrin fatty acid esters that are the oil gelators are soluble in oil and ester compounds of a linear or branched, saturated or unsaturated fatty acid(s) having 8 to 24 carbon atoms (preferably 14 to 18 carbon atoms) with a dextrin(s) having average degree of polymerization of 10 to 50 (preferably 20 to 30).

They include dextrin palmitic acid, palmitic acid/2-ethylhexanoic acid dextrin, dextrin stearic acid, palmitic acid/stearic acid dextrin, dextrin oleic acid, dextrin isopalmitic acid and dextrin isostearic acid. One or more kinds selected from the above can be used.

The marketed products of dextrin palmitic acid are, for example, trade name: Leopal KL, produced by Chiba Seifun Co., Ltd. and trade name: Leopal TL, produced by Chiba Seifun Co., Ltd. Further, the market products of palmitic acid/2-ethylhexanoic acid dextrin include trade name: Leopal TT, produced by Chiba Seifun Co., Ltd.

As for sucrose fatty acid esters that are the oil gelators, any sucrose fatty acid esters that are usually used in the cosmetic compositions are usable, and particularly it is preferable to use fatty acid esters of palmitic acid, stearic acid, behenic acid, oleic acid and lauric acid.

Metal soaps that are the oil gelators include isostearic acid aluminium, stearic acid aluminium and stearic acid calcium, and one or more kinds of these can be used.

As for anhydrous silicic acids that are the oil gelators, if they are those that are usually used in the cosmetic compositions, any forms of fumy, porous, non-porous, and spherical ones can be used. It is possible to use one or more kinds selected from the above. It is particularly preferable to use a fumy anhydrous silicic acid or a hydrophobized fumy anhydrous silicic acid that are obtained by treating fumy anhydrous silicic acid with hydrophobizing treatment.

In addition, a primary particle size of the fumy anhydrous silicic acid or hydrophobized fumy anhydrous silicic acid is preferably 50 nm or smaller, and particularly preferably 20 nm or smaller. The fumy anhydrous silicic acid can be obtained by hydrolyzing silicon tetrachloride in hydrogen and enzymatic salts.

The marketed products of the anhydrous silicic acid are, for example, products of Nippon Aerosil Co., Ltd. (Aerosil 50, Aerosil 130, Aerosil 200, Aerosil 200V, Aerosil 200CF, Aerosil 200FAD, Aerosil 300, Aerosil 300CF and Aerosil 380).

The hydrophobizing methods of the fumy anhydrous silicic acid are, for example, trimethylsiloxy treatment with trimethyl chlorosialane and hexamethyldisilazane, octyl silanization, coating and baking using methylhydrogen polysiloxane, and coating with metal soaps.

Examples of the marketed products of the hydrophobized fumy anhydrous silicic acid are products of Nippon Aerosil Co., Ltd. (Aerosil R-972, Aerosil R-972V, Aerosil R-972CF, Aerosil R-974, Aerosil R-976S, Aerosil RX200, Aerosil RY200, Aerosil R-202, Aerosil R-805, Aerosil R-812, Aerosil RA200H); a product of Talco Co.: Taranox 500; and a product of Cabot Corporation: CAB-O-SIL TS-530.

(Behenic acid/eicosanic diacid) glyceryl that is the oil gelling agent is an oligomer ester of behenic acid and eicosanic diacid with glycerin. The marketed products thereof are, for example, trade name: Nomcort HK-G, by the Nisshin OilliO Group, Ltd.

Examples of organically modified clay minerals that are the oil gelling agents include organically modified bentonites and those wherein water swell clay minerals are treated with quaternary ammonium salts. It is possible to use one or more kinds of the above. The marketed products of the organically modified bentonites are, for example, trade name: bentone 38, by NL Industries, Inc. and trade name: bentone 27 by NL Industries, Inc.

It is preferable to use oil gelling agents that are solid at room temperature to solid makeup compositions such as rouge, lipsticks and stick foundation, and waxes are especially preferable. This is because waxes can work their solidifying function well in the products of the present invention, and shape-retaining ability is sufficiently obtained in a small additive amount.

The content of the liquid ester compositions in the solid makeup compositions is preferably 3 to 90 mass %, more preferably 5 to 80 mass %, further more preferably 10 to 50 mass % and most preferably 20 to 30 mass %. Meanwhile, the content of the oil gelling agents in the solid makeup compositions is preferably 2 to 30 mass %, more preferably 5 to 25 mass %, and most preferably 5 to 20 mass %. When the content is within the above range, shape retaining ability and sense of use are further improved, and products can be obtained, wherein the gloss of cosmetic film is further improved and makeup lasts longer.

Besides, in the pasted makeup compositions such as liquid rouges and liquid eye shadow, it is preferable to use one or more kinds of oil gelling agent(s) selected from the group consisting of 12-hydroxystearic acid, dextrin fatty acid esters, sucrose fatty acid esters, metal soaps, anhydrous silicic acids, (behenic acid/eicosanic diacid) glyceryl and organically modified clay minerals.

The content of the liquid ester compositions in the pasted makeup compositions is preferably 3 to 90 mass %, more preferably 5 to 80 mass %, further more preferably 10 to 50 mass % and most preferably 10 to 30 mass %. Meanwhile, the content of the oil gelling agents in the pasted makeup compositions is preferably 0.001 to 10 mass %, more preferably 0.1 to 5 mass %, and most preferably 0.3 to 3 mass %. When the content is within the above range, shape retaining ability and sense of use are further improved, and the products can be obtained, wherein the gloss of cosmetic film is further improved and the makeup lasts longer.

The cosmetic compositions containing the liquid ester compositions of the present invention can be produced by publicly known methods for producing cosmetic compositions, except that the liquid ester compositions are used as raw materials.

Further, the make-up compositions containing the liquid ester compositions of the present invention and oil gelling agents can be produced by publicly known methods for producing makeup compositions, except that the liquid ester compositions and oil gelling agents are used as raw materials.

Next, the liquid ester compositions of the present invention can be used as lasting agents of cosmetic film.

This is because the liquid ester compositions of the present invention have a high viscosity of 100,000 mPa·s or higher, and adhesion ability of the cosmetic film to skin is high. As a result, the compositions have an effect of sustaining cosmetic film and can make makeup last longer. The liquid ester compositions of the present invention can be lasting agents of cosmetic film by itself or combined with one or more kinds of other components such as liquid fats and oils, liquid waxes, liquid hydrocarbon oils, liquid higher fatty acids, liquid higher alcohols, isopropanol, liquid ester oils, silicon oils, antioxidants and ultraviolet absorbers. Here, the liquid components indicate those that are liquid at room temperature. As for the liquid fats and oils, isopropanol, silicon oils, antioxidants and ultraviolet absorbers, the same ones can be used as those mentioned in the cosmetic compositions containing the liquid ester compositions. As for the liquid waxes, liquid hydrocarbon oils, liquid higher fatty acids, liquid higher alcohols and liquid ester oils, the liquid components at room temperature can be used among those mentioned in the cosmetic compositions containing the liquid ester compositions.

The content of the liquid ester compositions of the present invention in the lasting agents of cosmetic film is preferably 50 to 100 mass %, more preferably 70 to 100 mass % and most preferably 80 to 100 mass %.

The lasting agents of cosmetic film of the present invention can be used in the cosmetic compositions such as cosmetic compositions for makeup, emulsions, cream, sunscreen agents and cosmetic compositions for hair. The cosmetic compositions for makeup and hair are the same ones as those mentioned in the cosmetic compositions containing the liquid ester compositions.

The liquid ester compositions of the present invention can sustain feeling of cosmetic film and improve shape-retaining ability of lipsticks and the like. Therefore, cosmetic compositions for makeup, emulsions, cream, sunscreen agents and cosmetic compositions for hair that have an excellently long-lasting makeup can be provided by using the liquid ester compositions of the present invention.

Besides, since the liquid ester compositions of the present invention have pigment dispersibility, they can stably disperse pigments in the cosmetic compositions. In addition, since the liquid ester compositions of the present invention also have hydrating ability, they can provide gloss and moisture feeling to oily cosmetic compositions.

EXAMPLES

Examples will further illustrate the present invention in detail. The following Examples only explain the present invention and do not particularly limit the invention.

Production Example 1

Production of a Liquid Ester Composition 1, which is Obtained by Esterifying Dipentaerythritol with 2-(1,3,3-trimethyl)butyl-5,7,7-trimethyl octanoic acid 279 g (1.1 mol) of dipentaerythritol [trade name: Dipentaerythritol produced by Koei Chemical Company, Ltd.] and 1874 g (6.6 mol) of 2-(1,3,3-trimethyl)butyl-5,7,7-trimethyl octanoic acid [trade name: Isostearic Acid produced by Nissan Chemical Industries, Ltd.] were charged (mass ratio of set raw materials=10:67.2) into a 3L four-neck flask with a stirrer, thermometer, nitrogen gas blowing tube and water separation tube. Then, 0.1 mass % of dibutyltin oxide (catalyst) to a total set amount and 5 mass % of xylene (reflux solvent) to a total set amount were added thereto and reacted at 200 to 250° C. for about 36 hours while stirring. After completion of the reaction, xylene, a reflux solvent, was removed under reduced pressure. The reactant from which xylene was removed was subjected to the adsorption treatment by the activated earth, cooled down to around 60° C. and filtered. Then, the reactant was deodorized and distilled by ordinary methods to obtain 1399 g of a liquid ester composition 1.

The acid value of the liquid ester composition 1 was 0.3; hydroxyl value thereof was 32; both its freezing point and cloud point were not more than −30° C.; and its viscosity at 25° C. was 180,000 mPa·s. The viscosity was determined by a Brookfield viscosimeter (BH type) with a rotor No. 6 at 25° C. and rotation speed of 4 rpm.

Production Example 2

Production of a Liquid Ester Composition 2, which is Obtained by Esterifying Dipentaerythritol with 2-(1,3,3-trimethyl)butyl-5,7,7-trimethyl octanoic acid 58.4 g (0.23 mol) of dipentaerythritol [trade name: Dipentaerythritol produced by Koei Chemical Company, Ltd.] and 293.9 g (1.03 mol) of 2-(1,3,3-trimethyl)butyl-5,7,7-trimethyl octanoic acid [trade name: Isostearic Acid produced by Nissan Chemical Industries, Ltd.] were charged (mass ratio of set raw materials=10:50.3) into a 3L four-neck flask with a stirrer, thermometer, nitrogen gas blowing tube and water separation tube. Then, 0.05 mass % of dibutyltin oxide (catalyst) to a total set amount and 5 mass % of xylene (reflux solvent) to a total set amount were added thereto and reacted at 200 to 250° C. for about 21 hours while stirring. After completion of the reaction, xylene, a reflux solvent, was removed under reduced pressure. The reactant from which xylene was removed was treated with the adsorption treatment by the activated earth, cooled down to around 60° C. and filtered. Then, the reactant was deodorized and distilled by ordinary methods to obtain 245 g of a liquid ester composition 2.

The acid value of the liquid ester composition 2 was 0.2; hydroxyl value thereof was 81; its freezing point was −16° C. and it did not cloud even at −30° C.; and its viscosity at 25° C. was 350,000 mPa·s. The viscosity was determined by a Brookfield viscosimeter (BH type) with a rotor No. 6 at 25° C. and rotation speed of 2 rpm.

Production Example 3

Production of a Liquid Ester Composition 3, which is Obtained by Esterifying Dipentaerythritol with 2-(1,3,3-trimethyl)butyl-5,7,7-trimethyl octanoic acid 63.5 g (0.25 mol) of dipentaerythritol [trade name: Dipentaerythritol produced by Koei Chemical Company, Ltd.] and 248.5 g (0.88 mol) of 2-(1,3,3-trimethyl)butyl-5,7,7-trimethyl octanoic acid [trade name: Isostearic Acid produced by Nissan Chemical Industries, Ltd.] were charged (mass ratio of set raw materials=10:39.1) into a 3L four-neck flask with a stirrer, thermometer, nitrogen gas blowing tube and water separation tube. Then, 0.05 mass % of dibutyltin oxide (catalyst) to a total set amount and 5 mass % of xylene (reflux solvent) to a total set amount were added thereto and reacted at 200 to 250° C. for about 14 hours while stirring. After completion of the reaction, xylene, a reflux solvent, was removed under reduced pressure. The reactant from which xylene was removed was treated with the adsorption treatment by the activated earth, cooled down to around 60° C. and filtered. Then, the reactant was deodorized and distilled by ordinary methods to obtain 185 g of a liquid ester composition 3.

The acid value of the liquid ester composition 3 was 0.2; hydroxyl value thereof was 140; its freezing point was −12° C. and it did not cloud even at −30° C.; and its viscosity at 25° C. was 1,580,000 mPa·s. The viscosity was determined by a Brookfield viscosimeter (BH type) with a rotor No. 7 at 25° C. and rotation speed of 2 rpm.

Comparative Production Example 1

Production of a Comparative Liquid Ester Composition 1, which is Obtained by Esterifying Pentaerythritol with 2-(1,3,3-trimethyl)butyl-5,7,7-trimethyl octanoic acid 32.6 g (0.24 mol) of pentaerythritol [trade name: Pentaerythritol produced by Perstorp Group] and 286.3 g (1.01 mol) of 2-(1,3,3-trimethyl)butyl-5,7,7-trimethyl octanoic acid [trade name: Isostearic Acid produced by Nissan Chemical Industries, Ltd.] were charged into a 3L four-neck flask with a stirrer, thermometer, nitrogen gas blowing tube and water separation tube. Then, 0.1 mass % of dibutyltin oxide (catalyst) to a total set amount and 5 mass % of xylene (reflux solvent) to a total set amount were added thereto and reacted at 200 to 250° C. for about 28 hours while stirring. After completion of the reaction, xylene, a reflux solvent, was removed under reduced pressure. The reactant from which xylene was removed was treated with the adsorption treatment by the activated earth, cooled down to around 60° C. and filtered. Then, the reactant was deodorized and distilled by ordinary methods to obtain 251 g of a comparative liquid ester composition 1.

The acid value of the comparative liquid ester composition 1 was 0.3; hydroxyl value thereof was 10; both its freezing point and cloud point were not more than −30° C.; and its viscosity at 25° C. was 35,000 mPa·s. The viscosity was determined by a Brookfield viscosimeter (BH type) with a rotor No. 3 at 25° C. and rotation speed of 2 rpm.

Comparative Production Example 2

Production of a Comparative Pasted Liquid Ester Composition 2, which is obtained by Esterifying Dipentaerythritol with 2-(1,3,3-trimethyl)butyl-5,7,7-trimethyl octanoic acid 63.5 g (0.25 mol) of dipentaerythritol [trade name: Dipentaerythritol produced by Koei Chemical Company, Ltd.] and 218.9 g (0.75 mol) of 2-(1,3,3-trimethyl)butyl-5,7,7-trimethyl octanoic acid [trade name: Isostearic Acid produced by Nissan Chemical Industries, Ltd.] were charged (mass ratio of set raw materials=10:34.5) into a 3L four-neck flask with a stirrer, thermometer, nitrogen gas blowing tube and water separation tube. Then, 0.03 mass % of dibutyltin oxide (catalyst) to a total set amount and 5 mass % of xylene (reflux solvent) to a total set amount were added thereto and reacted at 200 to 250° C. for about 12 hours while stirring. After completion of the reaction, xylene, a reflux solvent, was removed under reduced pressure. The obtained reactant from which xylene was removed contained a high content of solid insoluble substances at 100° C., and it became a lacteous pasted semisolid substance at 50° C. Thus, purification by adsorption, deodorization and distillation treatments could not be conducted to the reactant and, therefore, a comparative pasted liquid ester composition 2 could not be obtained. Meanwhile, the acid value of the lacteous pasted semisolid substance was 8, and hydroxyl value thereof was 175.

Evaluations of pigment dispersibility, hydrating ability and compatibility with various oil solvents were made to the liquid ester compositions obtained in Production Examples 1 to 3 and Comparative Production Example 1. The evaluation methods and results thereof are described as follows.

[Samples of the Pigment Dispersibility Evaluation and the Evaluation Method Thereof]

1. Evaluated Samples

The evaluation was made to the liquid ester compositions 1 to 3, comparative liquid ester composition 1, diisostearyl malate (trade name: Cosmole 222 produced by the Nisshin OilliO Group, Ltd.), diglyceryl triisostearate using an isostearic acid that has the same branched structure as those of the liquid ester compositions 1 to 3 (trade name: Cosmole 43N produced by the Nisshin OilliO Group, Ltd.), hydrogenated polybutene (trade name: Parleam 24 produced by NOF Corporation) and liquid paraffin (trade name: Silkool P-70 produced by Matsumura Oil Co., Ltd.).

2. Evaluation Method 4 g of an evaluated sample and 16 g of liquid paraffin (trade name: Silkool P-70 produced by Matsumura Oil Co., Ltd.) as an oil diluent were collected to a calibrated and corked test tube, heated up to 80° C. and mixed uniformly. Next, 4 g of titanic oxide (trade name: TIPAQUE CR-50 produced by Ishihara Sangyo Kaisha, Ltd.), which is a pigment, was added to the obtained mixture and forcibly dispersed by shaking the mixture up and down by hand at room temperature for about 5 minutes. Then, the mixture was put into a thermostat bath kept at 40° C., left at rest and stored. One hour later, the pigment dispersion state thereof was observed and evaluated.

The evaluation of the pigment dispersibility was conducted by measuring length (mm) of the transparent separate phase of oil, which is produced on the upper part of a pigment dispersion liquid caused by sedimentation of pigments. Further, liquid paraffin was used as an evaluation sample, and put into a thermostat bath kept at 40° C., left at rest and stored for 24 hours. The length of 100 mm of the transparent separate phase of oil, which is produced on the upper part of a pigment dispersion liquid is regarded as a sedimentation rate of 100%. The sedimentation rate after one hour was calculated from the following formula and the evaluation was conducted based on the judgment standard shown in Table 1. Here, A=length (mm) from the liquid level after leaving an evaluated sample at rest at 40° C. for one hour; and B=length (100 mm) from the liquid level that transparently separated after leaving an evaluated sample that was dispersed in liquid paraffin only at rest, and storing it at 40° C. for 24 hours.

Sedimentation rate (%)=A/B×100

TABLE 1

| Evaluation Standards of Pigment Dispersibility | |
|---|---|
| Sedimentation rate (%) after one hour leaving at 40° C. | Indication of evaluation |
| Less than 1% | ⊚ |
| 1% or higher and less than 10% | ○ |
| 10% or higher and less than 30% | Δ |
| 30% or higher | X |

[Results of the Pigment Dispersibility Evaluation]

The results of the pigment dispersibility evaluation are shown in Table 2. As clarified from the results, the liquid ester compositions 1 to 3 are excellent in dispersibility of titanic oxide that is an inorganic pigment, which is typically regarded as being difficult to maintain the dispersion state. In contrast, the dispersibility of titanic oxide was not satisfactory in the comparative liquid ester composition 1, diglyceryl triisostearate using an isostearic acid that has the same branched structure as those of the liquid ester compositions 1 to 3, and diisostearyl malate generally used as a raw material of cosmetic compositions. As for hydrogenated polybutene, no dispersibility was seen.

TABLE 2

| Evaluation Results of Pigment Dispersibility | |
|---|---|
| Evaluated Samples | Evaluation Results |
| Liquid ester composition 1 | ⊚ |
| Liquid ester composition 2 | ○ |
| Liquid ester composition 3 | ○ |
| Comp. liquid ester composition 1 | Δ |
| Diisostearyl malate | Δ |
| Diglyceryl triisostearate | Δ |
| Hydrogenated polybutene | X |
| Liquid paraffin | X |

[Samples of the Hydrating Ability Evaluation and the Evaluation Method Thereof]

1. Evaluated Samples

The evaluation was made to the liquid ester compositions 1 to 3, comparative liquid ester composition 1, diisostearyl malate (trade name: Cosmole 222 produced by the Nisshin OilliO Group, Ltd.), diglyceryl triisostearate using an isostearic acid that has the same branched structure as those of the liquid ester compositions 1 to 3 (trade name: Cosmole 43N produced by the Nisshin OilliO Group, Ltd.), hydrogenated polybutene (trade name: Parleam 24 produced by NOF Corporation) and Vaseline (trade name: Nomcort W produced by the Nisshin OilliO Group, Ltd.).

2. Evaluation Method

The evaluation of hydrating ability was made based on the values obtained by measuring the water absorption capacity in accordance with the measurement of water absorption capacity of lanolin in the British Pharmacopoeia. The specific evaluation method is described as follows.

1 g of an evaluated sample and 9 g of Vaseline (trade name: Nomcort W produced by the Nisshin OilliO Group, Ltd.) as an oil diluent were collected to a 100 mL stainless beaker, heated up to 80° C., and dissolved and mixed uniformly to prepare a uniform sample. Next, the obtained sample was cooled down to room temperature and Vaseline-like solidification thereof was confirmed. Then, 0.1 to 0.5 g at a time of purified water was added dropwise to 10 g of the sample in a thermostat bath kept at 40° C. The purified water was kneaded with stirring by a stainless propeller(s), and the end-point was determined when purified water could not be kneaded into the sample.

The water absorption capacity (mass %) of an evaluated sample was calculated from the following formula and the evaluation of hydrating ability was conducted based on the evaluation standard shown in Table 3. Meanwhile, the hydrating ability was evaluated as high when the sample had a high value of the water absorption capacity (the standard is 100% or higher).

Water absorption capacity (%)=A total additive amount (g) of purified water/weight of the sample (10 g)×100

TABLE 3

Evaluation Standards of Hydrating Ability

| Water absorption capacity (%) of the sample | Indication of evaluation |
| --- | --- |
| 100% or higher | ○ |
| 40% or higher and not higher than 100% | Δ |
| Not higher than 40% | X |

[Results of the Hydrating Ability Evaluation]

The results of the hydrating ability evaluation are shown in Table 4. As clarified from the results, the liquid ester compositions 1 to 3 obtained in the present invention had a high water absorption capacity just as diglyceryl triisostearate using an isostearic acid that has the same branched structure as those of the liquid ester compositions 1 to 3 did, and, therefore, they had an excellent hydrating ability. In contrast, the water absorption capacities were low in the comparative liquid ester composition 1 wherein pentaerythritol was used instead of dipentaerythritol and diisostearyl malate generally used as a raw material of cosmetic compositions, and, therefore, their hydrating abilities were not satisfactory. As for hydrogenated polybutene, no hydrating ability was seen.

TABLE 4

Evaluation Results of Hydrating Ability

| Evaluated Samples | Evaluation Results |
| --- | --- |
| Liquid ester composition 1 | ○ |
| Liquid ester composition 2 | ○ |
| Liquid ester composition 3 | ○ |
| Comp. liquid ester composition 1 | Δ |
| Diisostearyl malate | Δ |
| Diglyceryl triisostearate | ○ |
| Hydrogenated polybutene | X |
| Nomcort W | X |

[Samples of the Compatibility Evaluation with Various Oil Solvents and the Evaluation Method Thereof]

1. Evaluated Samples

The evaluation was made to the liquid ester compositions 1 to 3, comparative liquid ester composition 1, diisostearyl malate (trade name: Cosmole 222 produced by the Nisshin OilliO Group, Ltd.), diglyceryl triisostearate using an isostearic acid that has the same branched structure as those of the liquid ester compositions 1 to 3 (trade name: Cosmole 43N produced by the Nisshin OilliO Group, Ltd.) and hydrogenated polybutene (trade name: Parleam 24 produced by NOF Corporation).

2. Evaluation Method 10 g of an evaluated sample and 10 g of various oil solvents ((1) isopropanol, (2) castor oil, (3) glyceryl tri2-ethylhexanoate, (4) liquid paraffin and (5) 10 cs dimethylsiloxane) were collected to a corked sample bottle, heated up to 70° C. and forcibly mixed by shaking the mixture up and down by hand for about 5 minutes. Then, the mixture was put into a thermostat bath, left at rest and stored for 15 minutes. After warming the reactant to room temperature, it was left at rest for 2 days. Then, its appearance was observed and the evaluation was made based on the judgment standard shown in Table 5.

TABLE 5

Evaluation Standards of Compatibility

| Status of the liquid mixture after 2 days | Indication of evaluation |
| --- | --- |
| Transparently compatible | ○ |
| Clouded or separated | X |

[Results of the Compatibility Evaluation with Various Oil Solvents]

The results of the compatibility evaluation with various oil solvents are shown in Table 6. As clarified from the results, the liquid ester compositions 1 to 3 in the present invention uniformly mutually dissolved in all of the oil solvents (1) to (4). Therefore, it was clarified that they could be formulated into various cosmetic compositions. Particularly, since the liquid ester composition 1 mutually dissolves with dimethylsiloxane having a low viscosity of the oil solvent (5), it can be formulated into skin care products containing dimethylsiloxane having a low viscosity and foundation.

Besides, since the liquid ester compositions 1 to 3 have a high compatibility with isopropanol, they can be used as a raw material for the surface treatment of powders, and the surface treated powders using the liquid ester compositions can be used in the cosmetic compositions.

On the other hand, as the comparative liquid ester composition 1 and hydrogenated polybutene do not have compatibility with castor oil, in case of formulating them into the cosmetic compositions, ingenuity is required such as combining with the other raw material(s). Therefore, it was clarified that use thereof was limited in respect of formulation.

Meanwhile, in the table, the oil solvent (1) is isopropanol (produced by Wako Pure Chemical Industries, Ltd.); the oil solvent (2) is castor oil (trade name: Purified Castor Oil, produced by Hokoku Corporation); the oil solvent (3) is glyceryl tri2-ethylhexanoate (trade name: T.I.O. produced by the Nisshin OilliO Group, Ltd.); the oil solvent (4) is liquid paraffin (trade name: Silkool P-70 produced by Matsumura Oil Co., Ltd.); and the oil solvent (5) is 10 cs dimethylsiloxane (trade name: KF-96 10CS produced by Shin-Etsu Chemical Co., Ltd.).

TABLE 6

Evaluation Results of Compatibility with Various Oil Solvents

| Evaluated Samples | Oil Solvents | | | | |
|---|---|---|---|---|---|
| | (1) | (2) | (3) | (4) | (5) |
| Liquid ester composition 1 | ○ | ○ | ○ | ○ | ○ |
| Liquid ester composition 2 | ○ | ○ | ○ | ○ | X |
| Liquid ester composition 3 | ○ | ○ | ○ | ○ | X |
| Comp. liquid ester composition 1 | ○ | X | ○ | ○ | ○ |
| Diisostearyl malate | X | ○ | ○ | ○ | ○ |
| Diglyceryl triisostearate | X | ○ | ○ | ○ | ○ |
| Hydrogenated polybutene | X | X | ○ | ○ | X |

Examples 1 to 6, and Comparative Example 1 to 7

[Preparation of Liquid Lip Gloss]

Liquid lip gloss was produced in formulations shown in Tables 7 to 10. First, components 1 to 8 were uniformly mixed at 90 to 105° C. to form a lasting agents of cosmetic film. A component 9 was dissolved in the obtained lasting agents of cosmetic film with heating, a compound 10 was added thereto and uniformly mixed to obtain a mixture. Next, the obtained mixture was filled in a bottle container with a lipstick brush and cooled down to obtain liquid lip gloss.

Meanwhile, in the tables, the compound 5 is hydrogenated polybutene (trade name: Parleam 24 produced by NOF Corporation); the compound 6 is diglyceryl triisostearate (trade name: Cosmole 43N produced by the Nisshin OilliO Group, Ltd.); the compound 7 is diisostearyl malate (trade name: Cosmole 222 produced by the Nisshin OilliO Group, Ltd.), the compound 8 is olefin oligomer (trade name: Salacos HPD-C produced by the Nisshin OilliO Group, Ltd.); and the component 9 is (behenic acid/eicosanic diacid) glyceryl (trade name: Nomcort HK-G, by the Nisshin OilliO Group, Ltd.).

TABLE 7

Formulating amount of liquid lip gloss (mass %)

| | | Examples | | | |
|---|---|---|---|---|---|
| Component | Raw materials | 1 | 2 | 3 | 4 |
| 1 | Liquid ester composition 1 | 80 | 50 | | |
| 2 | Liquid ester composition 2 | | | 80 | 50 |
| 3 | Liquid ester composition 3 | | | | |
| 4 | Comp. liquid ester composition 1 | | | | |
| 5 | Hydrogenated polybutene | | | | |
| 6 | Diglyceryl triisostearate | | | | |
| 7 | Diisostearyl malate | | 30 | | 30 |
| 8 | Olefin oligomer | 17.5 | 16 | 17.5 | 16 |
| 9 | (behenic acid/ eicosanic diacid) glyceryl | 0.5 | 2 | 0.5 | 2 |
| 10 | Pearl-lustering agent | 2 | 2 | 2 | 2 |
| | Total | 100 | 100 | 100 | 100 |

TABLE 8

Formulating amount of liquid lip gloss (mass %)

| | | Examples | |
|---|---|---|---|
| Component | Raw materials | 5 | 6 |
| 1 | Liquid ester composition 1 | | |
| 2 | Liquid ester composition 2 | | |
| 3 | Liquid ester composition 3 | 80 | 50 |
| 4 | Comp. liquid ester composition 1 | | |
| 5 | Hydrogenated polybutene | | |
| 6 | Diglyceryl triisostearate | | |
| 7 | Diisostearyl malate | | 30 |
| 8 | Olefin oligomer | 17.5 | 16 |
| 9 | (behenic acid/eicosanic diacid) glyceryl | 0.5 | 2 |
| 10 | Pearl-lustering agent | 2 | 2 |
| | Total | 100 | 100 |

TABLE 9

Formulating amount of liquid lip gloss (mass %)

| | | Comp. Examples | | | |
|---|---|---|---|---|---|
| Component | Raw materials | 1 | 2 | 3 | 4 |
| 1 | Liquid ester composition 1 | | | | |
| 2 | Liquid ester composition 2 | | | | |
| 3 | Liquid ester composition 3 | | | | |
| 4 | Comp. liquid ester composition 1 | 80 | 50 | | |
| 5 | Hydrogenated polybutene | | | 80 | 50 |
| 6 | Diglyceryl triisostearate | | | | |
| 7 | Diisostearyl malate | | 30 | | 30 |
| 8 | Olefin oligomer | 17.5 | 16 | 17.5 | 16 |
| 9 | (behenic acid/eicosanic diacid) glyceryl | 0.5 | 2 | 0.5 | 2 |
| 10 | Pearl-lustering agent | 2 | 2 | 2 | 2 |
| | Total | 100 | 100 | 100 | 100 |

TABLE 10

Formulating amount of liquid lip gloss (mass %)

| | | Comp. Examples | | |
|---|---|---|---|---|
| Component | Raw materials | 5 | 6 | 7 |
| 1 | Liquid ester composition 1 | | | |
| 2 | Liquid ester composition 2 | | | |
| 3 | Liquid ester composition 3 | | | |

TABLE 10-continued

Formulating amount of liquid lip gloss (mass %)

|   |   | Comp. Examples | | |
|---|---|---|---|---|
| Component | Raw materials | 5 | 6 | 7 |
| 4 | Comp. liquid ester composition 1 | | | |
| 5 | Hydrogenated polybutene | | | |
| 6 | Diglyceryl triisostearate | 80 | 50 | |
| 7 | Diisostearyl malate | | 30 | 80 |
| 8 | Olefin oligomer | 17.5 | 16 | 17.5 |
| 9 | (behenic acid/eicosanic diacid) glyceryl | 0.5 | 2 | 0.5 |
| 10 | Pearl-lustering agent | 2 | 2 | 2 |
| | Total | 100 | 100 | 100 |

[Evaluation Method of Liquid Lip Gloss]

The sensory evaluation of the obtained liquid lip gloss was conducted on lastingness of cosmetic film, such as feeling of cosmetic film, gloss, moisture feeling, and sense of use in coating (stickiness, spreading and the like). Further, preservation of stability at high temperature was evaluated by storing the liquid lip gloss for 30 days at 50° C. The specific evaluation method is described as follows.

1. Method of Sensory Evaluation 10 panelists became subjects and the number of people in the 10 panelists who answered "good" on each evaluation item of feeling of cosmetic film; gloss of cosmetic film; and sense of use (stickiness and spreading) was counted, and the evaluation was made based on the judgment standard shown in Table 11.

TABLE 11

Evaluation Standards of the Sensory Evaluation

| Number of people who answered "good" | Indication of evaluation |
|---|---|
| 8 or more | ○ |
| 4 to 7 | Δ |
| 0 to 3 | X |

2. Stability

The obtained liquid lip gloss was stored in a thermostat bath kept at 50° C. The state thereof after one month was observed, and evaluated as ○ for those remaining the same; Δ for those wherein a small sign(s) of change was observed; and × for those wherein an obvious change(s) was observed.

[Evaluation Results of Liquid Lip Gloss]

The evaluation results of the liquid lip gloss are shown in Tables 12 to 15. As clarified from the results, the liquid lip gloss containing the liquid ester compositions 1 to 3 of the present invention is excellent in feeling of cosmetic film, gloss, moisture feeling, sense of use in coating, lastingness of cosmetic film and preservation of stability.

In contrast, the liquid lip gloss of comparative examples 1 and 2 using low viscosity liquid ester compositions and those of comparative examples 5 and 6 using ester compositions wherein a branched isostearic acid(s) is used as a raw material were not satisfactory in respect of feeling of cosmetic film, gloss, lastingness of cosmetic film and preservation of stability. The liquid lip gloss of comparative examples 3 and 4 using polybutene was not satisfactory in respect of sense of use such as stickiness.

Further, the liquid lip gloss of comparative example 7 using diisostearyl malate that is a general raw material of cosmetic compositions was not satisfactory in all evaluation item.

TABLE 12

Evaluation Results of Liquid Lip Gloss

| | Examples | | | |
|---|---|---|---|---|
| evaluation item | 1 | 2 | 3 | 4 |
| Feeling of cosmetic film | ○ | ○ | ○ | ○ |
| Gloss | ○ | ○ | ○ | ○ |
| Moisture feeling | ○ | ○ | ○ | ○ |
| Sense of use | ○ | ○ | ○ | ○ |
| Lastingness of 2 hours later | ○ | ○ | ○ | ○ |
| Preservation stability | ○ | ○ | ○ | ○ |

TABLE 13

Evaluation Results of Liquid Lip Gloss

| | Examples | |
|---|---|---|
| evaluation item | 5 | 6 |
| Feeling of cosmetic film | ○ | ○ |
| Gloss | ○ | ○ |
| Moisture feeling | ○ | ○ |
| Sense of use | Δ | ○ |
| Lastingness of 2 hours later | ○ | ○ |
| Preservation stability | ○ | ○ |

TABLE 14

Evaluation Results of Liquid Lip Gloss

| | Comp. Examples | | | |
|---|---|---|---|---|
| evaluation item | 1 | 2 | 3 | 4 |
| Feeling of cosmetic film | Δ | Δ | ○ | ○ |
| Gloss | Δ | Δ | ○ | ○ |
| Moisture feeling | X | Δ | Δ | Δ |
| Sense of use | ○ | ○ | Δ | Δ |
| Lastingness of 2 hours later | X | Δ | ○ | ○ |
| Preservation stability | X | X | Δ | ○ |

TABLE 15

Evaluation Results of Liquid Lip Gloss

| | Comp. Examples | | |
|---|---|---|---|
| evaluation item | 5 | 6 | 7 |
| Feeling of cosmetic film | Δ | Δ | Δ |
| Gloss | Δ | Δ | Δ |
| Moisture feeling | Δ | ○ | Δ |
| Sense of use | Δ | Δ | Δ |
| Lastingness of 2 hours later | X | Δ | X |
| Preservation stability | X | X | X |

Example 7

A Stick Lipstick

[Preparation of a Stick Lipstick and Evaluation Results Thereof]

A stick lipstick having formulation of Table 16 was produced in accordance with the following processes.

A. After components 1 to 11 are dissolved with heating at 110 to 120° C., components 12 to 15 are added thereto and uniformly mixed.
B. Components 16 and 17 are added to the mixture obtained in Process A and uniformly mixed with heating. After defoaming, the mixture is poured and filled in a mold and cooled down to mold.
C. The solidified substance molded in Process B is taken out of the mold and contained in a container to obtain a stick lipstick.

Though the obtained stick lipstick was taken out of the container and horizontally left at rest in a thermostat bath kept at 50° C. for one week, no change was seen and, therefore, it was excellent in shape retaining ability. In addition, its sense of use in coating was also good and it was also excellent in feeling of cosmetic film, gloss and moisture feeling. Thus, the obtained stick lipstick was satisfactory in respect of long-lastingness of makeup.

Meanwhile, the liquid ester composition 2 of the present invention was used as the compound 5 in Table 16, and for other components, products marketed as raw materials of cosmetic compositions were used.

TABLE 16

Formulation of a stick lipstick

| Component | Raw materials | Mass % |
|---|---|---|
| 1 | Ceresin wax | 8 |
| 2 | Microcrystalline wax | 5 |
| 3 | Paraffin | 4 |
| 4 | (Behenic acid/eicosanic diacid) glyceryl | 5 |
| 5 | Liquid ester composition 2 | 25 |
| 6 | Phytosteryl oleate | 5 |
| 7 | Diisostearyl malate | 25 |
| 8 | Octyl dodecanol | 5 |
| 9 | Vegetable squalane | 0.5 |
| 10 | Tri(capryl/capric acid) glyceryl ester | 10.8 |
| 11 | Isooctyl palmitate | 2.0 |
| 12 | Mica titanium | 3.0 |
| 13 | Red No. 104 | 0.4 |
| 14 | Blue No. 1 | 0.5 |
| 15 | Orange No. 201 | 0.2 |
| 16 | 2-ethylhexyl p-methoxycinnamate | 0.1 |
| 17 | Natural vitamin E | 0.5 |
| | Total | 100 |

Example 8

A Pasted Lipstick

[Preparation of a Pasted Lipstick and Evaluation Results Thereof]

A pasted lipstick having formulation of Table 17 was produced in accordance with the following processes.

A. After components 1 to 11 are uniformly dissolved with mixing under heating, components 12 to 17 are added thereto and uniformly mixed.
B. The mixture obtained in Process A is filled to obtain a pasted lipstick.

The obtained pasted lipstick had an excellent sense of use in coating, feeling of cosmetic film, gloss and moisture feeling. Thus, it was satisfactory in respect of long-lastingness of makeup. Further, there was no problem such as effluents, and its shape retaining ability was also good.

Meanwhile, in Table 17, a product produced by Chiba Seifun Co., Ltd.: Leopal TL was used as the component 2; a product produced by Nippon Aerosil Co., Ltd.: Aerosil R-976S was used as the component 3; the liquid ester composition 1 of the present invention was used as the component 5; and a product produced by the Nisshin OilliO Group, Ltd.: Salacos E-38 was used as the component 6. For other components, products marketed as raw materials of cosmetic compositions were used.

TABLE 17

Formulation of a pasted lipstick

| Component | Raw materials | Mass % |
|---|---|---|
| 1 | 12-hydroxystearic acid | 1 |
| 2 | Dextrin fatty acid ester | 3 |
| 3 | Dimethyldichlorosilane-treated fumy silica | 1 |
| 4 | Aluminum isostearate | 1 |
| 5 | Liquid ester composition 1 | 25 |
| 6 | Erythrityl tri2-ethylhexanoate | 10 |
| 7 | Propylene glycol dicaprate | 10 |
| 8 | Diglyceryl tetraisostearate | 20 |
| 9 | Diisostearyl malate | 23.8 |
| 10 | Oxybenzone | 0.1 |
| 11 | Natural vitamin E | 0.1 |
| 12 | Colcothar | 1.5 |
| 13 | Mica titanium | 1.5 |
| 14 | Red No. 202 | 0.1 |
| 15 | Yellow No.4 | 0.6 |
| 16 | Titanium oxide | 1.2 |
| 17 | Iron oxide black | 0.1 |
| | Total | 100 |

Example 9

A stick lip gloss

[Preparation of a Stick Lip Gloss and Evaluation Results Thereof]

A stick lip gloss having formulation of Table 18 was produced in accordance with the following processes.

A. After components 1 to 4 are dissolved with heating at 90° C., components 5 and 6 are added thereto and uniformly mixed.
B. A component 7 is added to the mixture obtained in Process A and uniformly mixed with heating. After defoaming, the mixture is poured and filled in a mold and cooled down to mold.
C. The solidified substance molded in Process B is taken out of the mold and contained in a container to obtain a stick lip gloss.

The obtained stick lip gloss had an excellent sense of use in coating, feeling of cosmetic film, gloss and moisture feeling. Thus, it was satisfactory in respect of long-lastingness of makeup. Further, its shape retaining ability was also good.

Meanwhile, in Table 18, the liquid ester composition 3 of the present invention was used as the compound 1, and a product produced by Chiba Seifun Co., Ltd.: Leopal KL was used as the component 2. For other components, products marketed as raw materials of cosmetic compositions were used.

TABLE 18

Formulation of a stick lip gloss

| Component | Raw materials | Mass % |
|---|---|---|
| 1 | Liquid ester composition 3 | 25 |
| 2 | Dextrin fatty acid ester | 10 |
| 3 | Liquid paraffin | 12.89 |
| 4 | Diisostearyl malate | 50 |
| 5 | Titanium oxide covered glass powder | 2 |
| 6 | Red No. 226 | 0.01 |
| 7 | Natural vitamin E | 0.1 |
| | Total | 100 |

Example 10

Solid Powder Foundation

[Preparation of a Solid Powder Foundation and Evaluation Results Thereof]

A solid powder foundation having formulation of Table 19 was produced in accordance with the following processes.

A. Components 10 to 12 are heated at 90° C. and mixed.
B. Components 1 to 9 are dispersed by mixing.
C. The mixture obtained in Process A is added to the mixture obtained in Process B and mixed.
D. The mixture obtained in Process C is ground and formed on the plate by compressing to obtain a solid powder foundation.

The obtained solid powder foundation had an excellent sense of use in coating, adhesion of cosmetic film and long-lastingness of makeup. Thus, it was satisfactory. Besides, even when the molded product was set to a container and carried out for one week, no crack or peeling off was seen. Therefore, it was also excellent in shape retaining ability.

Meanwhile, in Table 19, a product produced by Ganz Chemical Co., Ltd.: Ganzpearl GS-0605 was used as the component 9, and the liquid ester composition 1 of the present invention was used as the compound 12. For other components, products marketed as raw materials of cosmetic compositions were used.

TABLE 19

Formulation of a solid powder foundation

| Component | Raw materials | Mass % |
|---|---|---|
| 1 | Titanium oxide | 5 |
| 2 | Colcothar | 0.5 |
| 3 | Iron oxide yellow | 1.2 |
| 4 | Iron oxide black | 0.1 |
| 5 | Sericite | 52 |
| 6 | Mica | 20 |
| 7 | Talc | 4.7 |
| 8 | Methyl parahydroxybenzoate | 0.5 |
| 9 | Polystyrene (spherical 6 μm) | 2 |
| 10 | Dimethyl polysiloxane (20 cs) | 3 |
| 11 | Vegetable squalane | 8 |
| 12 | Liquid ester composition 1 | 3 |
| | Total | 100 |

Example 11

Emulsion

[Preparation of Emulsion and Evaluation Results Thereof]

Emulsion having formulation of Table 20 was produced in accordance with the following processes.

A. Components 1 to 6 are mixed at 80° C.
B. Components 7 to 13 are heated up to 80° C. and added to the mixture obtained in Process A for emulsifying.
C. The emulsified substance obtained in Process B is cooled down to obtain emulsion.

The obtained emulsion is satisfactory in lastingness of feeling of cosmetic film and moisture feeling.

Meanwhile, the liquid ester composition 1 of the present invention was used as the compound 3 in Table 20, and for other components, products marketed as raw materials of cosmetic compositions were used.

TABLE 20

Formulation of emulsion

| Component | Raw materials | Mass % |
|---|---|---|
| 1 | Sorbitan monooleate (HLB 4.3) | 0.1 |
| 2 | Polyoxyethylene sorbitan monostearate (20 E.O.) (HLB 14.9). | 2 |
| 3 | Liquid ester composition 1 | 6 |
| 4 | Octyldodecyl lactate | 4 |
| 5 | Flavoring agents | 0.02 |
| 6 | Glyceryl tri2-ethylhexanoate | 1 |
| 7 | Dipropylene glycol | 5 |
| 8 | Glycerin | 5 |
| 9 | Sodium alginate | 0.5 |
| 10 | Carboxyvinyl polymer | 0.2 |
| 11 | Ethyl parahydroxybenzoate | 0.1 |
| 12 | Purified water | 75.98 |
| 13 | Magnesium L-ascorbate phosphate | 0.1 |
| | Total | 100 |

Example 12

Liquid Foundation

[Preparation of Liquid Foundation and Evaluation Results Thereof]

Liquid foundation having formulation of Table 21 was produced in accordance with the following processes.

A. Components 10 to 17 are mixed with heating and cooled down to 40° C. Then, components 1 to 9 are added thereto and dispersed with a homomixer.
B. Components 18 to 23 are uniformly dissolved by mixing.
C. The mixture obtained in Process B is added to the dispersed substance obtained in Process A for emulsifying and liquid foundation is obtained.

The obtained liquid foundation had an excellent sense of use in coating and it was satisfactory in respect of feeling of cosmetic film, moisture feeling and long-lasting of makeup.

Meanwhile, in Table 21, the liquid ester composition 1 of the present invention was used as the component 10, and a product produced by Shin-Etsu Chemical Co., Ltd.: KF-6017 was used as the compound 16. For other components, products marketed as raw materials of cosmetic compositions were used.

TABLE 21

Formulation of liquid foundation

| Component | Raw materials | Mass % |
|---|---|---|
| 1 | Titanium oxide | 7 |
| 2 | Zinc oxide | 3 |
| 3 | Talc | 4.7 |
| 4 | Mica | 2 |
| 5 | Iron oxide red | 0.2 |
| 6 | Iron oxide yellow | 1.6 |
| 7 | Iron oxide black | 0.2 |
| 8 | Nylon | 2 |
| 9 | Mica titanium | 2 |
| 10 | Liquid ester composition 1 | 10 |
| 11 | Octyldodecyl lactate | 5 |
| 12 | Dimethyl polysiloxane (20 cs) | 5 |
| 13 | Octamethylcyclotetrasiloxane | 20 |
| 14 | Vegetable squalane | 1 |
| 15 | Cetyl isooctanoate | 2 |
| 16 | Polyoxyethylene methylpolysiloxane copolymer | 3 |
| 17 | Sorbitan sesquioleate | 1 |
| 18 | Purified water | 20 |
| 19 | Ethanol | 5 |
| 20 | Glycerin | 5 |
| 21 | Natural vitamin E | 0.1 |
| 22 | Hyaluronic acid | 0.1 |
| 23 | Flavoring agents | 0.1 |
| | Total | 100 |

Example 13

Hand Cream

[Preparation of Hand Cream and Evaluation Results Thereof]

Hand cream having formulation of Table 22 was produced in accordance with the following processes.

A. Components 1 to 7 are mixed and a component 8 is dispersed thereto with a disper mixer.
B. Component 9 to 12 are uniformly dissolved by mixing.
C. The mixture obtained in Process B is added to the dispersed substance obtained in Process A for emulsifying and water-in-oil hand cream is obtained.

The obtained hand cream had an excellent sense of use in coating, feeling of being coated and moisture feeling. It was also satisfactory in respect of long-lasting of makeup. Further, though it was left at rest in a thermostat bath kept at 40° C. for one month, no separation was seen and, therefore, it was confirmed that its stability was also high.

Meanwhile, in Table 22, the liquid ester composition 2 of the present invention was used as the component 4; a product produced by the Nisshin OilliO Group, Ltd.: Salacos E-38 was used as the component 5; and a product produced by Goldschmidt AG: ABIL EM-90 was used as the component 7. For other components, products marketed as raw materials of cosmetic compositions were used.

TABLE 22

Formulation of hand cream

| Component | Raw materials | Mass % |
|---|---|---|
| 1 | Vegetable squalane | 5 |
| 2 | Vaseline | 1 |
| 3 | Octamethylcyclopentasiloxane | 10 |
| 4 | Liquid ester composition 2 | 5 |
| 5 | Erythrityl tri2-ethylhexanoate | 25 |
| 6 | Cetyl isooctanoate | 10 |

TABLE 22-continued

Formulation of hand cream

| Component | Raw materials | Mass % |
|---|---|---|
| 7 | Alkyl containing polyoxyalkylene-modified organopolysiloxane | 3 |
| 8 | Silica | 3 |
| 9 | Ethanol | 5 |
| 10 | 1,3-butylene glycol | 5 |
| 11 | Purified water | 27.9 |
| 12 | Hyaluronic acid | 0.1 |
| | Total | 100 |

Example 14

A Sunscreen Agent

[Preparation of a Sunscreen Agent and Evaluation Results Thereof]

A sunscreen agent having formulation of Table 23 was produced in accordance with the following processes.

A. Components 1 to 12 are uniformly mixed.
B. Components 13 to 16 are uniformly mixed.
C. The mixture obtained in Process B is added to the dispersed substance obtained in Process A to emulsify.
D. The emulsified substance obtained in Process C is filled in a resin bottle with a stainless ball in it to obtain a sunscreen agent.

The obtained sunscreen agent had an excellent sense of use in coating, feeling of being coated and moisture feeling. It was also satisfactory in respect of long-lasting of makeup. Further, in observing the agent with a light microscope (1000 magnification) after leaving it at rest at room temperature for 24 hours, no aggregation of powders was seen. Therefore, its stability was also high since no appearance change was seen.

Meanwhile, in Table 23, the liquid ester composition 1 of the present invention was used as the component 1; a product produced by the Nisshin OilliO Group, Ltd.: Salacos E-38 was used as the component 2; a product produced by Ishihara Sangyo Kaisha, Ltd.: TIPAQUE TTO-S2 was used as the component 3; and a product produced by Goldschmidt AG: ABIL EM-90 was used as the component 8. For other components, products marketed as raw materials of cosmetic compositions were used.

TABLE 23

Formulation of a sunscreen agent

| Component | Raw materials | Mass % |
|---|---|---|
| 1 | Liquid ester composition 1 | 7 |
| 2 | Erythrityl tri2-ethylhexanoate | 5 |
| 3 | Titanium oxide treated with stearic acid | 10 |
| 4 | Decamethyl pentacyclosiloxane | 15 |
| 5 | 2-ethylhexyl p-methoxycinnamate | 5 |
| 6 | Neopentyl glycol dicaprate | 9.8 |
| 7 | Trimethoxysiloxy cinnamate | 2 |
| 8 | Alkyl containing polyoxyalkylene-modified organopolysiloxane | 3 |
| 9 | POE-sorbitan monooleate (20 mol) | 0.2 |
| 10 | Sorbitan sesquioleate | 0.8 |
| 11 | Nylon powder | 2 |
| 12 | Flavoring agents | 0.1 |
| 13 | 1,3-butylene glycol | 5 |

TABLE 23-continued

Formulation of a sunscreen agent

| Component | Raw materials | Mass % |
|---|---|---|
| 14 | Ethanol | 5 |
| 15 | Sodium chloride | 0.1 |
| 16 | Purified water | 30 |
| | Total | 100 |

Example 15

Eye Gloss

[Preparation of Eye Gloss and Evaluation Results Thereof]

Eye gloss having formulation of Table 24 was produced in accordance with the following processes.

A. Components 1 to 11 are uniformly dissolved with mixing under heating.

B. The mixture obtained in Process A is filled to obtain pasted eye gloss.

The obtained eye gloss had an excellent sense of use in coating, feeling of cosmetic film, gloss and moisture feeling. Thus, it was satisfactory in respect of long-lasting of makeup. Further, there were no property changes such as effluents and separation, and its shape retaining ability was also good.

Meanwhile, in Table 24, a product produced by Dai-Ichi Kogyo Seiyaku Co., Ltd.: Sugar Wax S-10E was used as the component 2; a product produced by NL Industries, Inc.: Bentone 27 was used as the component 3; the liquid ester composition 1 of the present invention was used as the component 6; and a product produced by the Nisshin OilliO Group, Ltd.: Salacos E-38 was used as the component 7. For other components, products marketed as raw materials of cosmetic compositions were used.

TABLE 24

Formulation of eye gloss

| Component | Raw materials | Mass % |
|---|---|---|
| 1 | (Behenic acid/eicosanic diacid) glyceryl | 2 |
| 2 | Sucrose fatty acid ester | 3 |
| 3 | Organically modified bentonite | 2 |
| 4 | Diisostearyl malate | 10 |
| 5 | Diglyceryl triisostearate | 25 |
| 6 | Liquid ester composition 1 | 10 |
| 7 | Erythrityl tri2-ethylhexanoate | 25 |
| 8 | Liquid lanolin | 10 |
| 9 | 2-ethylhexyl p-methoxycinnamate | 0.1 |
| 10 | 2,6-ditertiary-butyl paracresol | 0.1 |
| 11 | Glyceryl tri2-ethylhexanoate | 12.8 |
| | Total | 100 |

Example 16

Eye Shadow

[Preparation of Eye shadow and Evaluation Results Thereof]

Eye shadow having formulation of Table 25 was produced in accordance with following processes.

A. Components 1 to 7 are dissolved with heating at 90° C., and components 8 to 12 are added thereto and uniformly mixed.

B. Components 13 and 14 are added to the mixture obtained in Process A and uniformly mixed with heating. After defoaming, the mixture is filled into a container and cooled down to 5° C. to obtain a stick eye shadow.

The obtained eye shadow had an excellent sense of use in coating, feeling of cosmetic film, gloss and moisture feeling. Thus, it was satisfactory in respect of long-lasting of makeup. Further, its shape retaining ability was also good.

Meanwhile, the liquid ester composition 1 of the present invention was used as the compound 1 in Table 25, and for other components, products marketed as raw materials of cosmetic compositions were used.

TABLE 25

Formulation of eye shadow

| Component | Raw materials | Mass % |
|---|---|---|
| 1 | Liquid ester composition 1 | 20 |
| 2 | Phytosteryl oleate | 10 |
| 3 | Glyceryl tri2-ethylhexanoate | 9.8 |
| 4 | Dimethyl polysiloxane (100 cs) | 5 |
| 5 | Ceresin wax | 11 |
| 6 | Carnauba wax | 1 |
| 7 | Sorbitan sesquiisostearate | 2 |
| 8 | Titanium oxide | 3 |
| 9 | Mica titanium | 15 |
| 10 | Mica | 20 |
| 11 | Cobalt blue | 2 |
| 12 | Iron oxide black | 1 |
| 13 | Natural vitamin E | 0.1 |
| 14 | Flavoring agents | 0.1 |
| | Total | 100 |

Example 17

Hair Cream

[Preparation of Hair Cream and Evaluation Results Thereof]

Hair cream having formulation of Table 26 was produced in accordance with the following processes.

A. Components 1 to 4 are uniformly dissolved by mixing.

B. Components 5 to 9 and 11 are uniformly dissolved by mixing.

C. The mixture obtained in Process B are added to the mixture obtained in Process A at 80° C. for emulsifying. Then, a component 10 is added thereto and cooled down to obtain hair cream.

The obtained hair cream had an excellent sense of use in coating, gloss of cosmetic film and moisture feeling. Thus, it was satisfactory in respect of long-lasting of makeup. Further, no separation was seen after leaving it at rest at room temperature for one month and, therefore, stability was also high.

Meanwhile, in Table 26, the liquid ester composition 1 of the present invention was used as the compound 4, and a product produced by Nihon Emulsion Co., Ltd.: EMALEX 503 was used as the component 6. For other components, products marketed as raw materials of cosmetic compositions were used.

TABLE 26

Formulation of hair cream

| Component | Raw materials | Mass % |
|---|---|---|
| 1 | Dimethyl polysiloxane (6 cs) | 5 |
| 2 | Liquid paraffin | 9 |
| 3 | Cetyl isooctanoate | 13.5 |
| 4 | Liquid ester composition 1 | 2.5 |
| 5 | Behenyl alcohol | 4 |
| 6 | Polyoxyethylene oleyl ether | 1 |
| 7 | Propylene glycol | 7 |
| 8 | Sodium Pyroglutamate | 0.5 |
| 9 | Ethyl parahydroxybenzoate | 0.5 |
| 10 | Flavoring agents | 0.1 |
| 11 | Purified water | 56.9 |
|  | Total | 100 |

What is claimed is:

1. A liquid ester composition obtained by esterifying 2-(1,3,3-trimethyl)butyl-5,7,7-trimethyl octanoic acid with dipentaerythritol, said liquid ester composition having a viscosity at 25° C. of 100,000 to 2,000,000 mPa·s; hydroxyl value of 10 to 160; and cloud point of less than 5° C.

2. The liquid ester composition according to claim 1, which is obtained by esterifying dipentaerythritol with 2-(1,3,3-trimethyl)butyl-5,7,7-trimethyl octanoic acid in the mass ratio of 10:35 to 10:90 at 200 to 250° C. for 10 to 40 hours at the presence of a catalyst(s).

3. The liquid ester composition according to claim 2, wherein dipentaerythritol and 2-(1,3,3-trimethyl)butyl-5,7,7-trimethyl octanoic acid are used in the mass ratio of 10:39 to 10:72.

4. The liquid ester composition according to claim 1, wherein an acid value is 10 or lower.

5. The liquid ester composition according to claim 1, wherein a hydroxyl value is 20 to 140.

6. The liquid ester composition according to claim 1, wherein a cloud point is not more than 0° C.

7. A cosmetic composition which contains the liquid ester composition according to claim 1.

8. The cosmetic composition according to claim 7, wherein the cosmetic composition is one selected from the group consisting of cosmetic compositions for makeup, emulsions, cream, sunscreen agents and cosmetic compositions for hair.

9. A cosmetic composition for makeup which contains the liquid ester composition according to claim 1 and an oil gelling agent(s).

10. The cosmetic composition for makeup according to claim 9, wherein the cosmetic composition for makeup is solid and contains 3 to 90 mass % of the liquid ester composition and 2 to 30 mass % of the oil gelling agent(s).

11. The cosmetic composition for makeup according to claim 9, wherein the cosmetic composition for makeup is pasted and contains 3 to 90 mass % of the liquid ester composition and 0.001 to 10 mass % of the oil gelling agent(s).

12. A lasting agent of cosmetic film which contains the liquid ester composition according to claim 1.

13. The lasting agent of cosmetic film according to claim 12 that contains 50 to 100 mass % of the liquid ester composition.

* * * * *